US009526539B2

(12) United States Patent
Zwirkoski

(10) Patent No.: US 9,526,539 B2
(45) Date of Patent: Dec. 27, 2016

(54) NON-SOFT TISSUE REPAIR

(71) Applicant: SPINAL VENTURES, LLC, Brighton, MI (US)

(72) Inventor: Paul A. Zwirkoski, Pinckney, MI (US)

(73) Assignee: SPINAL VENTURES, LLC, Brighton, MI (US)

(*) Notice: Subject to any disclaimer, the term of this patent is extended or adjusted under 35 U.S.C. 154(b) by 0 days.

(21) Appl. No.: 14/265,000

(22) Filed: Apr. 29, 2014

(65) Prior Publication Data
US 2014/0249633 A1 Sep. 4, 2014

Related U.S. Application Data

(63) Continuation of application No. 12/616,843, filed on Nov. 12, 2005, now Pat. No. 8,734,520, which is a
(Continued)

(51) Int. Cl.
*A61F 2/44* (2006.01)
*A61B 17/70* (2006.01)
(Continued)

(52) U.S. Cl.
CPC ......... *A61B 17/7097* (2013.01); *A61B 17/686* (2013.01); *A61B 17/7094* (2013.01); *A61B 17/8635* (2013.01); *A61F 2/442* (2013.01); *A61F 2/4425* (2013.01); *A61F 2/46* (2013.01); *A61F 2/4611* (2013.01); *A61B 17/8863* (2013.01); *A61F 2/30749* (2013.01); *A61F 2002/2835* (2013.01); *A61F 2002/302* (2013.01);
(Continued)

(58) Field of Classification Search
CPC ........ A61F 2/441; A61F 2/46; A61F 2/30749; A61F 2002/4631; A61B 17/7097
USPC .................. 623/17.16, 16.11, 23.48; 606/105
See application file for complete search history.

(56) References Cited

U.S. PATENT DOCUMENTS 919,205 A 4/1909 Newhall
1,347,622 A 7/1920 Deininger
(Continued)

FOREIGN PATENT DOCUMENTS

DE 2 320 373 A1 11/1974
DE 26 51 441 A1 5/1978
(Continued)

OTHER PUBLICATIONS

MSDS Superelastic Nitinol Alloys; Nitinol Devices and Components.*
(Continued)

*Primary Examiner* — Ellen C Hammond
*Assistant Examiner* — Stuart S Bray
(74) *Attorney, Agent, or Firm* — Marshall, Gerstein & Borun LLP

(57) ABSTRACT

An implant for filling and/or distracting a body region, particularly a non-soft tissue cavity, has a plurality of segments wherein at least two of the segments are flexibly connected. The segments have a crush-strength sufficient to create and/or maintain the distraction of two or more non-soft tissue body surfaces, and to maintain the stability of the body region. The implant may be inserted into a cavity by an applicator having a cannula with a distal opening, and a rotary driver for applying force to move the implant within the cannula.

16 Claims, 25 Drawing Sheets

Related U.S. Application Data continuation of application No. 11/298,961, filed on Dec. 9, 2005, now Pat. No. 7,682,400, which is a continuation-in-part of application No. 10/866,219, filed on Jun. 10, 2004, now abandoned.

(51) Int. Cl.
*A61B 17/86* (2006.01)
*A61B 17/68* (2006.01)
*A61F 2/46* (2006.01)
*A61B 17/88* (2006.01)
*A61F 2/28* (2006.01)
*A61F 2/30* (2006.01)

(52) U.S. Cl.
CPC .............. *A61F 2002/30331* (2013.01); *A61F 2002/30383* (2013.01); *A61F 2002/30462* (2013.01); *A61F 2002/30495* (2013.01); *A61F 2002/30604* (2013.01); *A61F 2002/30662* (2013.01); *A61F 2002/30663* (2013.01); *A61F 2002/443* (2013.01); *A61F 2002/444* (2013.01); *A61F 2002/4415* (2013.01)

(56) References Cited

U.S. PATENT DOCUMENTS

| | | |
|---|---|---|
| 1,445,817 A | 2/1923 | Ballou, Jr. |
| 1,607,996 A | 11/1926 | Morgenthaler |
| 1,994,561 A | 3/1935 | Bostwick |
| 2,097,099 A | 10/1937 | Legat |
| 2,260,700 A | 10/1941 | Bloom et al. |
| 2,378,655 A | 6/1945 | Popp |
| 2,624,457 A | 1/1953 | Jablon |
| 2,659,396 A | 11/1953 | Gledhill et al. |
| 2,668,710 A | 2/1954 | Carlson |
| 3,023,471 A | 3/1962 | Nabuda |
| 3,170,311 A | 2/1965 | Raphael |
| 3,385,050 A | 5/1968 | Hall |
| 3,386,240 A | 6/1968 | Blumstein |
| 3,590,519 A | 7/1971 | Spilhaus |
| 3,639,137 A * | 2/1972 | Marinelli ............ F16B 15/0092 411/548 |
| 3,780,400 A | 12/1973 | Hinsperger |
| 3,846,846 A | 11/1974 | Fischer |
| 3,882,858 A | 5/1975 | Klemm |
| 4,038,703 A | 8/1977 | Bokros |
| 4,191,740 A | 3/1980 | Heusser et al. |
| 4,286,360 A | 9/1981 | Skobel |
| 4,430,033 A | 2/1984 | McKewan |
| 4,514,125 A | 4/1985 | Stol |
| 4,566,832 A | 1/1986 | Mirsberger et al. |
| 4,654,017 A | 3/1987 | Stein |
| 4,702,454 A | 10/1987 | Izumida |
| 4,752,170 A | 6/1988 | McSherry et al. |
| 4,969,888 A | 11/1990 | Scholten et al. |
| 5,084,050 A | 1/1992 | Draenert |
| 5,108,404 A | 4/1992 | Scholten et al. |
| 5,133,755 A * | 7/1992 | Brekke .................. A61F 2/28 623/23.51 |
| 5,161,296 A | 11/1992 | Garfield et al. |
| 5,171,280 A | 12/1992 | Baumgartner |
| 5,192,326 A | 3/1993 | Bao et al. |
| 5,339,618 A | 8/1994 | Sawyer |
| 5,372,146 A * | 12/1994 | Branch .............. A61B 17/0401 128/898 |
| 5,423,829 A | 6/1995 | Pham et al. |
| 5,505,736 A | 4/1996 | Reimels et al. |
| 5,520,691 A | 5/1996 | Branch |
| 5,534,023 A * | 7/1996 | Henley .................. A61F 2/12 623/7 |
| 5,538,514 A | 7/1996 | Hawkins |
| 5,669,931 A | 9/1997 | Kupiecki et al. |
| 5,702,454 A | 12/1997 | Baumgartner |
| 5,716,359 A | 2/1998 | Ojima et al. |
| 5,749,894 A | 5/1998 | Engelson |
| 5,755,797 A * | 5/1998 | Baumgartner .......... A61F 2/441 623/17.16 |
| 5,756,127 A * | 5/1998 | Grisoni ................ A61K 9/0024 424/426 |
| 5,769,898 A | 6/1998 | Jisander |
| 5,824,093 A | 10/1998 | Ray et al. |
| 5,827,289 A | 10/1998 | Reiley et al. |
| 5,849,004 A | 12/1998 | Bramlet |
| 5,861,043 A | 1/1999 | Carn |
| 5,906,632 A | 5/1999 | Bolton |
| 5,938,385 A | 8/1999 | Garfield et al. |
| 5,958,465 A | 9/1999 | Klemm et al. |
| 5,964,797 A | 10/1999 | Ho |
| 5,983,385 A | 11/1999 | Khayrallah et al. |
| 5,984,926 A | 11/1999 | Jones |
| 6,048,346 A | 4/2000 | Reiley et al. |
| 6,165,218 A | 12/2000 | Husson et al. |
| 6,183,768 B1 | 2/2001 | Harle |
| 6,231,615 B1 | 5/2001 | Preissman |
| 6,245,107 B1 | 6/2001 | Ferree |
| 6,251,143 B1 | 6/2001 | Schwartz et al. |
| 6,280,475 B1 | 8/2001 | Bao et al. |
| 6,280,477 B1 | 8/2001 | Mastrorio et al. |
| 6,299,448 B1 | 10/2001 | Zdrahala et al. |
| 6,348,055 B1 | 2/2002 | Preissman |
| 6,383,188 B2 | 5/2002 | Kuslich et al. |
| 6,383,190 B1 | 5/2002 | Preissman |
| 6,387,130 B1 | 5/2002 | Stone et al. |
| 6,395,007 B1 | 5/2002 | Bhatnagar et al. |
| 6,520,635 B1 | 2/2003 | Ignatowski |
| 6,562,033 B2 | 5/2003 | Shah et al. |
| 6,579,533 B1 | 6/2003 | Tormala et al. |
| 6,595,998 B2 | 7/2003 | Johnson et al. |
| 6,616,673 B1 * | 9/2003 | Stone ................... A61B 17/025 606/105 |
| 6,620,162 B2 | 9/2003 | Kuslich et al. |
| 6,620,169 B1 | 9/2003 | Peterson et al. |
| 6,620,196 B1 * | 9/2003 | Trieu ..................... A61F 2/441 623/17.16 |
| 6,632,245 B2 | 10/2003 | Kim |
| 6,663,647 B2 | 12/2003 | Reiley et al. |
| 6,712,853 B2 | 3/2004 | Kuslich |
| 6,713,083 B1 | 3/2004 | McGregor et al. |
| 6,746,483 B1 | 6/2004 | Bojarski et al. |
| 6,773,450 B2 | 8/2004 | Leung et al. |
| 6,860,691 B2 | 3/2005 | Unsworth et al. |
| 6,960,215 B2 | 11/2005 | Olson, Jr. et al. |
| 7,001,124 B2 | 2/2006 | Panasik et al. |
| 7,025,771 B2 | 4/2006 | Kuslich et al. |
| 7,056,345 B2 | 6/2006 | Kuslich |
| 7,220,282 B2 | 5/2007 | Kuslich |
| 7,226,481 B2 | 6/2007 | Kuslich |
| 7,261,720 B2 | 8/2007 | Stevens et al. |
| 7,309,357 B2 | 12/2007 | Kim |
| 7,682,400 B2 | 3/2010 | Zwirkoski |
| 7,789,912 B2 | 9/2010 | Manzi et al. |
| 7,879,041 B2 | 2/2011 | Rabiner et al. |
| 8,012,155 B2 | 9/2011 | Prygoski et al. |
| 8,070,797 B2 * | 12/2011 | Flanagan ............... A61L 31/082 623/1.1 |
| 8,163,031 B2 | 4/2012 | Truckai et al. |
| 8,377,136 B2 * | 2/2013 | Simonton ............... A61F 2/442 623/17.11 |
| 8,613,942 B2 | 12/2013 | Vogt et al. |
| 2002/0068974 A1 | 6/2002 | Kuslich et al. |
| 2002/0099408 A1 * | 7/2002 | Marks .............. A61B 17/12022 606/200 |
| 2002/0147496 A1 | 10/2002 | Belef et al. |
| 2002/0147497 A1 | 10/2002 | Belef et al. |
| 2002/0183761 A1 | 12/2002 | Johnson et al. |
| 2002/0184739 A1 | 12/2002 | Taubner et al. |
| 2003/0028251 A1 | 2/2003 | Mathews |
| 2003/0110798 A1 | 6/2003 | Ignatowski |
| 2003/0121150 A1 | 7/2003 | Pratt |
| 2003/0141327 A1 | 7/2003 | Cruise et al. |
| 2003/0158557 A1 | 8/2003 | Cragg et al. |
| 2003/0229372 A1 | 12/2003 | Reiley et al. |

(56) References Cited

U.S. PATENT DOCUMENTS

| | | | |
|---|---|---|---|
| 2004/0010314 A1 | 1/2004 | Matsuzaki et al. | |
| 2004/0014568 A1 | 1/2004 | Williams et al. | |
| 2004/0033212 A1 | 2/2004 | Thomson et al. | |
| 2004/0097930 A1 | 5/2004 | Justis et al. | |
| 2004/0138758 A1* | 7/2004 | Evans | A61L 27/12 623/23.51 |
| 2004/0176854 A1 | 9/2004 | Hesseling et al. | |
| 2004/0220669 A1 | 11/2004 | Studer | |
| 2004/0249464 A1 | 12/2004 | Bindseil et al. | |
| 2005/0022556 A1 | 2/2005 | Zhou et al. | |
| 2005/0113903 A1* | 5/2005 | Rosenthal | A61F 2/90 623/1.15 |
| 2005/0131541 A1* | 6/2005 | Trieu | A61F 2/441 623/17.11 |
| 2005/0278023 A1 | 12/2005 | Zwirkoski | |
| 2007/0006612 A1 | 1/2007 | Ignatowski | |
| 2007/0055271 A1 | 3/2007 | Schaller | |
| 2007/0055272 A1 | 3/2007 | Schaller | |
| 2007/0055273 A1 | 3/2007 | Schaller | |
| 2007/0055274 A1 | 3/2007 | Appenzeller et al. | |
| 2007/0055275 A1 | 3/2007 | Schaller | |
| 2007/0093822 A1 | 4/2007 | Dutoit et al. | |
| 2007/0093906 A1 | 4/2007 | Hudgins et al. | |
| 2007/0299455 A1 | 12/2007 | Stevens et al. | |
| 2008/0119945 A1 | 5/2008 | Frigg | |
| 2010/0076497 A1 | 3/2010 | Zwirkoski | |
| 2011/0079757 A1 | 4/2011 | Manvel | |
| 2012/0031572 A1 | 2/2012 | Ng et al. | |
| 2012/0094794 A1 | 4/2012 | Ng | |
| 2012/0255326 A1 | 10/2012 | Prestwidge | |
| 2013/0014351 A1* | 1/2013 | Kuglen | B65D 63/1027 24/17 B |
| 2013/0062905 A1 | 3/2013 | Held | |
| 2013/0066373 A1 | 3/2013 | Liao | |
| 2013/0079186 A1 | 3/2013 | Lin | |
| 2013/0247336 A1* | 9/2013 | Chou | E06B 9/326 24/116 A |
| 2013/0312362 A1 | 11/2013 | Maanum et al. | |

FOREIGN PATENT DOCUMENTS

| | | |
|---|---|---|
| DE | 38 09 571 | 4/1989 |
| DE | 197 10 392 C1 | 7/1999 |
| EP | 0 621 020 | 10/1994 |
| WO | WO-82/03174 A1 | 9/1982 |
| WO | WO-00/54821 A1 | 9/2000 |
| WO | WO-02/30338 A1 | 4/2002 |
| WO | WO-02/43628 | 6/2002 |
| WO | WO-02/47563 | 6/2002 |
| WO | WO-02/071921 | 9/2002 |
| WO | WO-03/007854 | 1/2003 |
| WO | WO-03/059180 | 7/2003 |
| WO | WO-2005/122956 A2 | 12/2005 |

OTHER PUBLICATIONS

International Search Report Application No. PCT/US03/26615, dated Jul. 22, 2005.

International Preliminary Report on Patentability for Application No. PCT/US05/20476, dated Aug. 4, 2006.

International Search Report for Application No. PCT/US05/20476, dated Apr. 6, 2006.

Kirkpatrick et al., "In Vitro Characteristics of Tobramycin-PMMA Beads: Compressive Strength and Leaching," *Orthopedics*, 8(9):1130-1133 (1985).

Office Action for U.S. Appl. No. 11/298,961, dated Sep. 2, 2009.

Office Action for U.S. Appl. No. 11/298,961, dated Dec. 8, 2008.

Supplementary European Search Report for Application No. EP05853727, dated Sep. 23, 2013.

European Search Opinion for Application No. EP05853727, dated Sep. 23, 2013.

International Search Report for Application No. PCT/US2005/044879, dated Jun. 10, 2008.

Written Opinion for Application No. PCT/US2005/44879, dated Jun. 10, 2008.

TOGGLER® Anchor System, Technical Bulletin—ALLIGATOR® Solid-Wall Anchors© 2008, 2010, 2012.

OptiMesh® 1500DS—Spineology® brochure, Aug. 2009.

\* cited by examiner

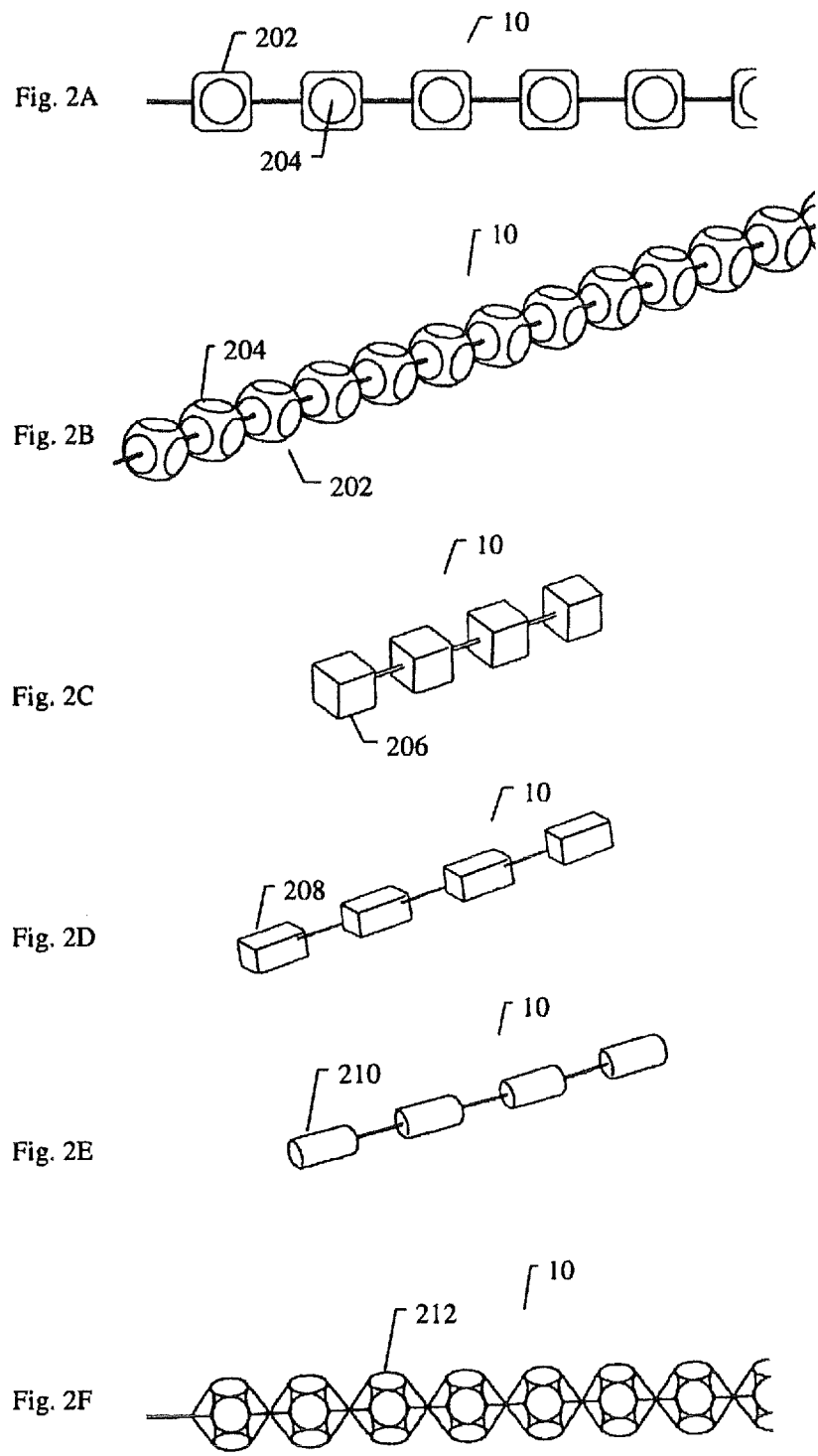

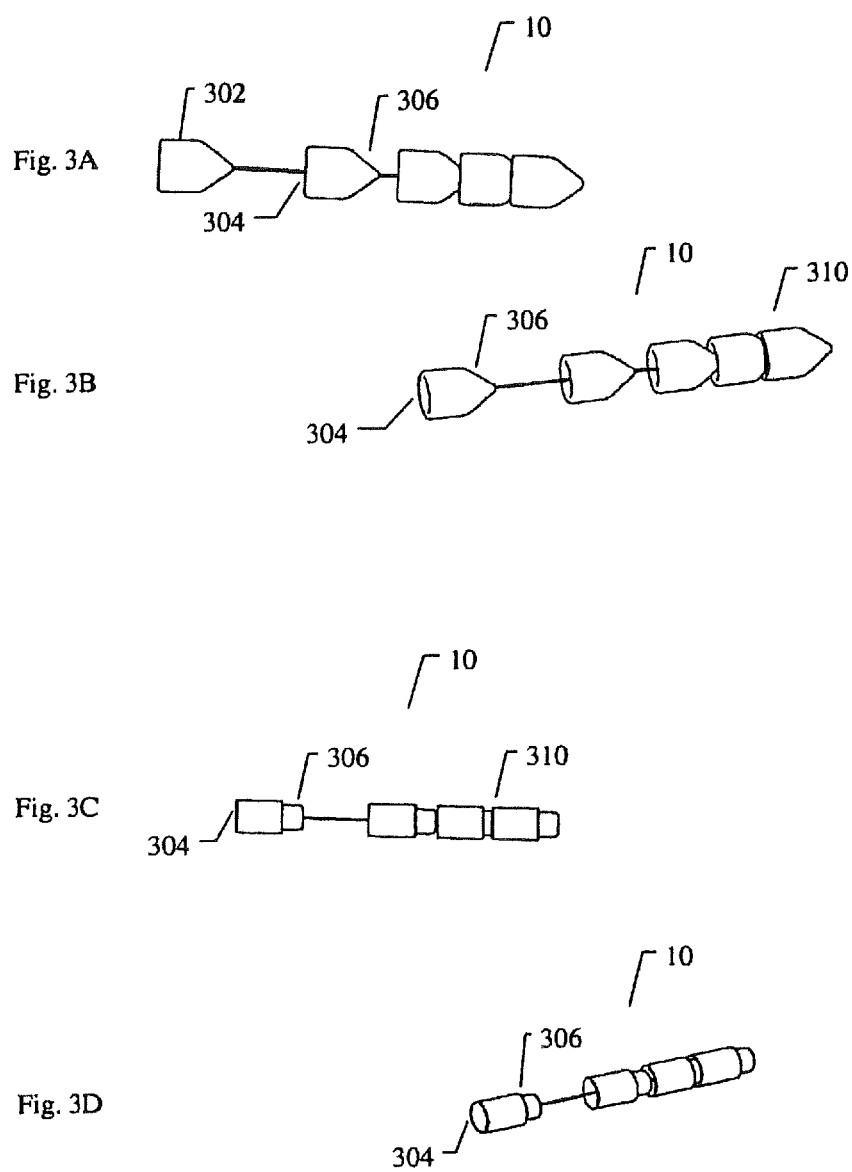

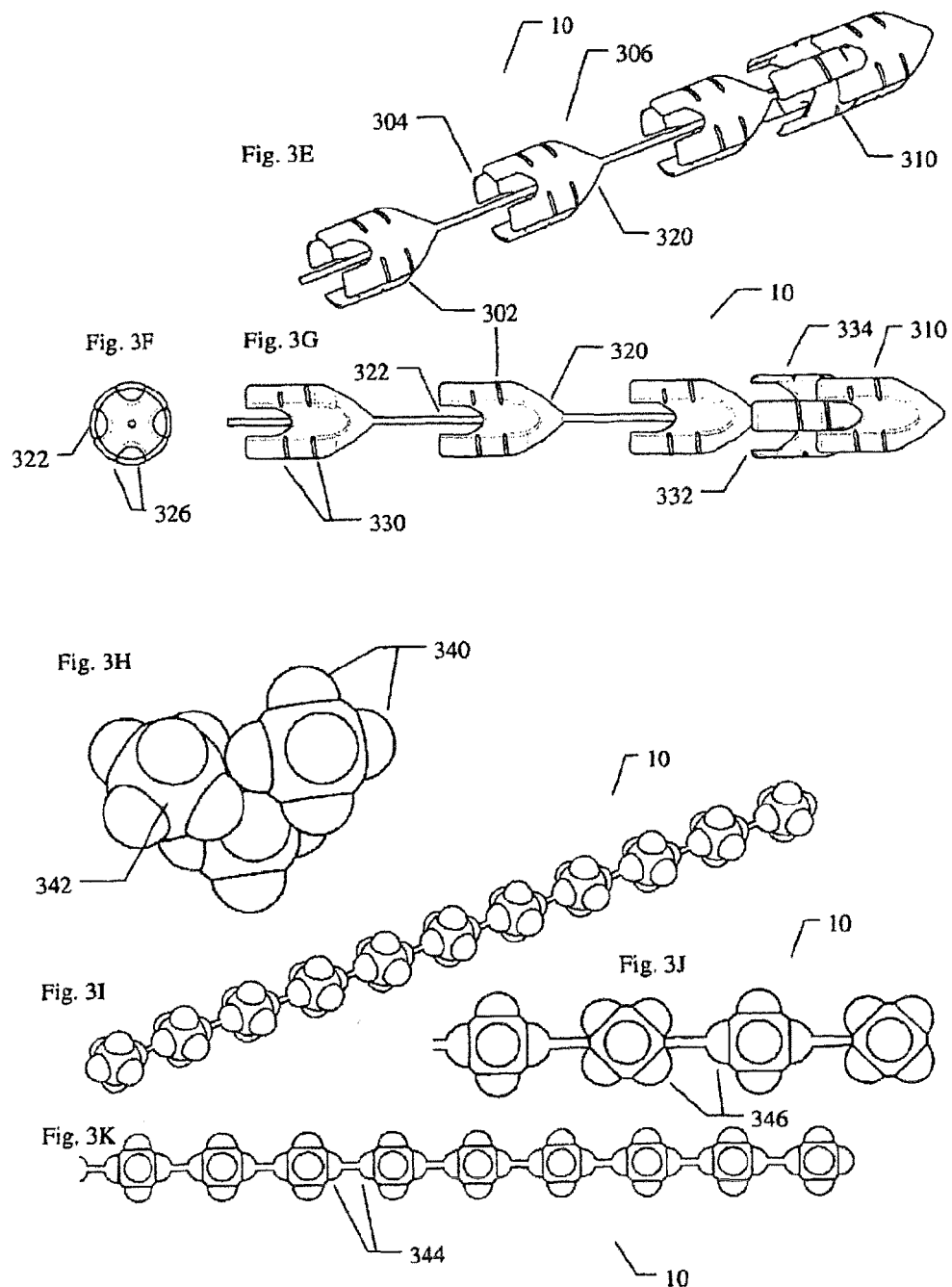

Fig. 7A
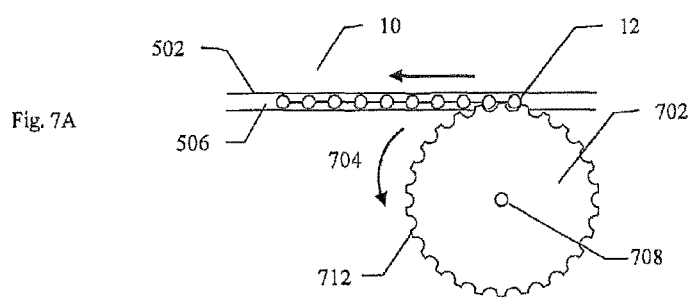
Fig. 7B
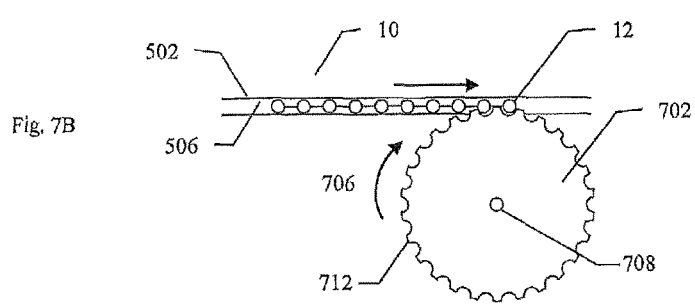
Fig. 7C
Fig. 7D
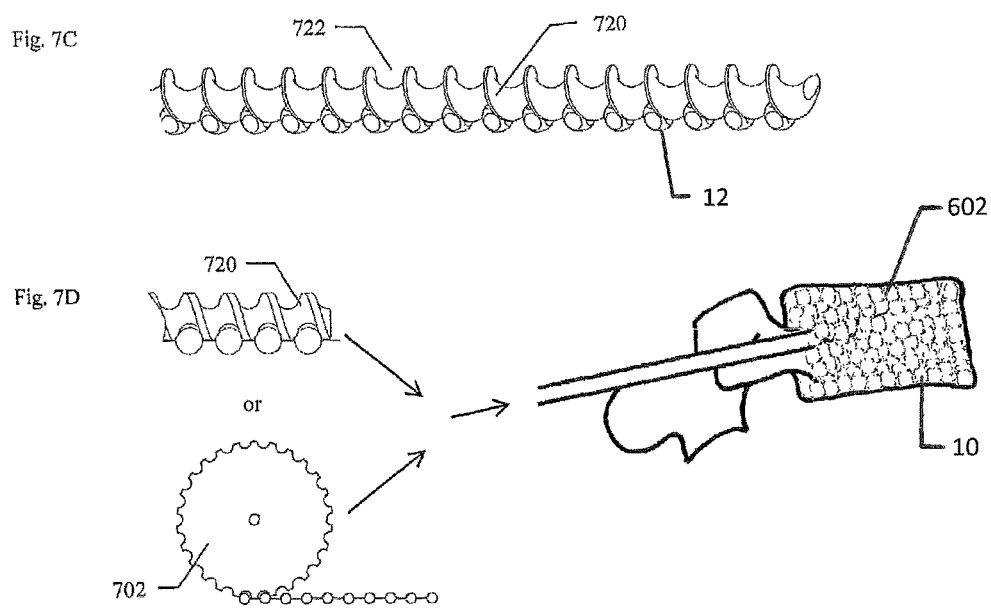

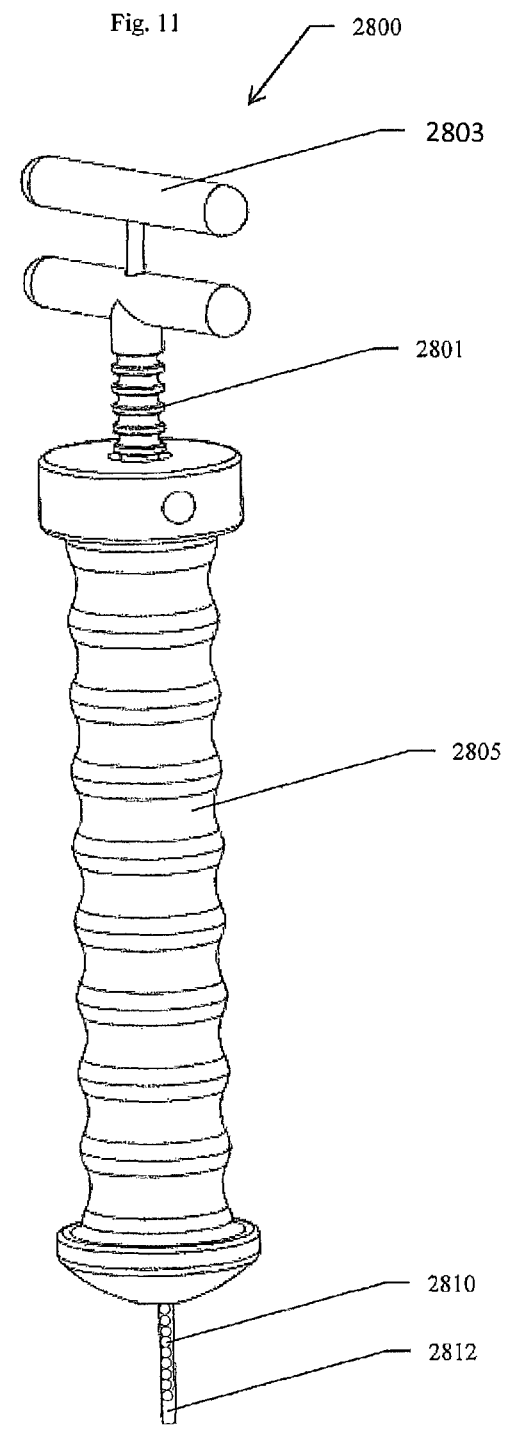

NON-SOFT TISSUE REPAIR

CROSS-REFERENCE TO RELATED APPLICATIONS

This application is a continuation of U.S. application Ser. No. 12/616,843, filed on Nov. 12, 2009, which is a continuation of U.S. application Ser. No. 11/298,961, filed on Dec. 9, 2005, now U.S. Pat. No. 7,682,400, which is a continuation-in-part of U.S. application Ser. No. 10/866,219, filed on Jun. 10, 2004, now abandoned, the disclosures of which are herein incorporated by reference.

FIELD

Described here are tissue cavity implants, implant applicators, delivery devices, and methods for using them. In particular, the description relates to implants having a plurality of flexibly connected segments having a strength sufficient to support, to fill, to create, to maintain, to distract, or to otherwise repair a portion of the spine, including a bone cavity such as might be found in a fractured vertebral body, or the intervertebral region of the spine, and methods and devices for inserting these implants.

BACKGROUND

Proper treatment of spinal injuries such as trauma, fractures, non-unions, tumors, cysts, and degenerated discs may involve filling a cavity that has been created by the pathology itself or by the action of a surgeon. Often the cavities are compressed, and require that the surfaces of the cavity be distracted from one another and then supported to return the spinal structure to its anatomic position and form. Furthermore, because spinal tissues such as vertebra and cartilage have structural and support roles in the body, it is critical that such cavities be repaired to allow reliable strength and support.

Compression fractures are one type of hard tissue injury belonging to a class of conditions that may be treated using devices and methods for separating, distracting, and supporting a fractured bone. For example, vertebral compression fractures are crushing injuries to one or more vertebra. A vertebral compression injury may be the result of a trauma to the spine, an underlying medical condition, or a combination of a trauma and an underlying condition. Osteoporosis and metastatic cancers are common medical conditions that also contribute to vertebral compression fractures because they weaken spinal bone, predisposing it to compressive injury.

Osteoporosis is a degenerative disease that reduces bone density, and makes bone more prone to fractures such as compression fractures. An osteoporosis-weakened bone can collapse during even normal activity. According to the National Institute of Health, vertebral compression fractures are the most common type of osteoporotic fractures.

Vertebral fractures may be painful and may deform the shape of the spine, resulting in unhealthy pressure on other parts of the body, loss of height, and changes in the body's center of gravity. Untreated, such changes and the resulting discomfort can become permanent, since the bone heals without expanding the compression.

Existing methods of treating bone injuries may involve highly invasive or inadequate treatments. For example, one method of treatment is percutaneous vertebroplasty. Vertebroplasty involves injecting bone filler (such as bone cement) into the collapsed vertebra to stabilize and strengthen the crushed bone. In vertebroplasty, physicians typically insert a small diameter guide wire or needle along the pedicle path intended for the bone filler delivery needle. The guide wire is advanced into the vertebral body under fluoroscopic guidance to the delivery point within the vertebrae. The access channel into the vertebra may be enlarged to accommodate the delivery tube. In some cases, the delivery tube is placed directly into a vertebral body and forms its own opening. In other cases, an access cannula is placed over the guide wire and advanced into the vertebral body. In both cases, a hollow needle or similar tube is placed into the vertebral body and used to deliver the bone filler into the vertebra.

When filling a bone cavity with bone filler using traditional vertebroplasty, fillers with lower viscosities may leak. Further, even fillers having low viscosities may require the application of a high pressure to disperse the bone filler throughout the vertebral body. However, application of high pressure also increases the risk of bone filler extravasation from the vertebral body. Conversely, injecting a bone filler having a higher viscosity may provide an even greater risk of "leaking" bone filler into sensitive adjacent body areas. Leaks or extrusion of the bone filler may be dangerous to a patient's health. For example, posterior extravasation from a vertebral body may cause spinal cord trauma, perhaps resulting in paralysis. Risk of leakage is even more acute when a bone filler is applied under pressure to expand a compression fracture, especially if the fracture has begun healing and requires substantial force to distract the cavity surfaces.

Furthermore, most bone cements and bone fillers are difficult to remove or to adjust. Removal and adjustment may be important when distracting a bone cavity. For example, removing a precise amount of bone filler may allow a surgeon to adjust the level of distraction of a vertebral compression fracture and correct the shape of the compressed bone. Many bone cements, once set, are difficult or impossible to remove without further, highly invasive, surgery. Even if the removal is attempted prior to the expiration of the setting time, the materials may have non-Newtonian flow characteristics requiring a substantial removal vacuum to achieve an initial and sudden movement.

The implants described herein may avoid many of the problems described above when filling a cavity within the body, and particularly a cavity within the spinal region. The use of segments contained within a flexible tube or sheath offers an alternative to packing or expanding a cavity within body tissue. This could be an advantage in the treatment cavities such as vertebral compression fractures since the use of a flexible tube reduces concerns of fluent material leakage from the internal vertebral space and provides more control in delivery. These devices may be used in other regions of the body where the filling of a cavity with stability and control is desired, and is not necessarily limited to the spinal region. For example, the devices described herein may be used to repair hip; tibia, and other areas of bone displacement.

In addition to traditional bone cements, a handful of other cavity filling materials have been suggested. In particular, biodegradable and/or bioabsorbable devices have been suggested. For example, U.S. Pat. No. 5,756,127 to Grisoni et al. describes a bioresorbable string of calcium sulfate hemihydrate (Plaster of Paris) beads and a means for producing these beads. However, the Grisoni device is not appropriate for spinal regions, and has many disadvantages. Calcium sulfate hemihydrate (Plaster of Paris) and similar materials have low elasticity and crush strength, making them unreliable as materials to distract and later support a spinal region, particularly during the early stages of the healing process. Filling materials that are readily compressed or crushed may shift within, or exit, the cavity altogether, leading to detrimental changes in the shape of the spinal region. Materials with low crush strength are poor choices in withstanding the stress of distracting spinal regions, and may be unable to maintain the distracted shape after filling a spinal region. Similar materials are the subjects of U.S. Pat. No. 6,579,533 to Tormala et al.

U.S. Pat. No. 5,702,454 to Baumgartner describes an implant made of an elastic plastic for implanting into an intervertebral disk. Because the Baumgartner implant is elastic and somewhat amorphic, it may be less effective for filling and distracting spinal cavities, particularly cavities benefiting from implants having some stiffness, such as non-soft tissue cavities, and cavities that benefit from a stable implant shape. This is particularly true where sustained distraction is desired.

U.S. Pat. No. 6,595,998 to Johnson et al. describes a tissue distraction device in which wafers are inserted to distract a tissue cavity by forming a wafer stack within the cavity. However, Johnson's column of wafers is not amenable to providing uniform support to all surfaces of a cavity, when such support is needed. For example, a tissue cavity supported or distracted on all sides of the cavity may be more stable.

U.S. Pat. No. 5,958,465 to Klemm et al. describes a method and apparatus for making drug-containing implants in the form of a string of beads comprising chains of small drug-containing plastic bodies arranged in series on a surgical wire or thread. Similar drug implanted beads-on-a-string are described in U.S. Pat. No. 6,183,768 to Harle and German Patents 2320373 to Klemm and 2651441 to Heusser. The Klemm, Harle, and Heusser implants are designed for drug delivery, and are embedded with one or more drugs which are released from the plastic (e.g. PMMA) beads (also called "corpuscles"). Thus, these implants may be limited in strength and durability because of the inclusion of a releasable drug, as well as the properties and shape of the implant beads.

In any event, none of the cited documents show the device and methods disclosed below. The devices described herein may address many of the problems identified above, particularly in the treatment of the spine.

BRIEF SUMMARY

Broadly, described here are segmented implants for filling a tissue cavity, applicators for inserting implants, and methods of using the segmented implants and applicators to fill and/or distract tissue cavities. In particular, the implants described here may be used for filling and/or distracting non-soft tissue cavities such as a bone cavity, and for anchoring devices (e.g., bone screws, etc.) within the body. Generally, the segmented implants described here comprise a plurality of segments, which can be arranged as a linear array. The implant may also include a flexible elongate tube having an inner region. The plurality of segments may be arranged within the inner region of the elongate tube in a linear array. The implant is configured to fill a cavity within a non-soft body region (such as bone).

The implant may include a second (or more) outer tube surrounding the first flexible, elongate tube. The implant may also include a fluent material within any part of the implant (e.g., within the first flexible tube, between the first and second flexible tube, within the segments, etc.). The fluent material may be a settable fluent material that can harden (e.g., a cement). In some variations, the settable material is activated by applying energy, or other catalyst. For example, the fluent material may be catalyzed to harden by applying electromagnetic energy (e.g., UV light), heat, or a chemical catalyst (e.g., hardener). Any of the tubes of the implant (e.g., the first flexible tube) may be at least partially porous and configured to pass fluent material from within the first flexible elongate tube.

In some variation, the segments are flexibly connected by a filament. The segments may also interlock (e.g., they may have shapes that communicate with each other).

Also described herein are implants for insertion into a non-soft body region, comprising a first flexible elongate tube having an inner region, a second, flexible elongate tube having an inner region (wherein the second flexible elongate tube is at least partly contained within the first flexible elongate tube) and a plurality (e.g., a linear array) of segments within the inner region of the second flexible elongate tube. In some variations, the implant also includes a settable fluent material contained between the first and second flexible elongate tubes. The settable material may be catalyzed to harden, as described above.

Also described herein are implants for insertion into a non-soft body region comprising a first flexible elongate tube having an inner region, a plurality of segments within the inner region of the first flexible elongate tube, a fluent material within the inner region of the first flexible elongate tube, and a transmission path configured to transmit electromagnetic energy to harden the fluent material. The transmission path may be any appropriate path for transmitting energy (e.g., a fiberoptic line, an electrical conductor, etc.). In some variations, the transmission path comprises the segments (e.g., which may be transparent or conductive for electromagnetic energy).

Also described are methods of filling a cavity within a body. The method may include the steps of inserting an implant into a cavity (wherein the implant comprises a first flexible elongate tube having an inner region and a plurality of segments within the inner region of the first flexible elongate tube), and activating a fluent material within the implant to harden the fluent material. The method may also include the step of adding a settable fluent material to the implant. The step of activating the fluent material may comprises applying electromagnetic energy to the fluent material (e.g., UV light), or applying a catalyst (e.g., a hardener).

The method may also include the step of inserting a second implant into the cavity, wherein the second implant comprises an flexible elongate tube having an inner region and a plurality of segments within the inner region of the flexible elongate tube. In some variations, an second implant may be inserted into a first implant either before, during or after insertion into a body cavity.

Also described herein are applicators for use with an implant having flexibly connected segments. The applicator may include an inner cannula having a channel configured to hold at least a portion of the implant, a stiff member having a releasable engagement region configured to engage at least some of the segments of the implant (wherein the stiff member is slideably and rotatably coupled to the channel of the inner cannula), and an outer sheath surrounding at least a portion of the inner cannula.

In some variations, the applicator further comprising a handle attached to the stiff member. The handle may be configured to be manipulated to engage the releasable engagement region of the stiff member with the implant. The applicator may also include a lock for securing the stiff member within the channel of the inner cannula so that the stiff member may not slide within the inner cannula. The lock may be a locking pin.

The outer sheath of the applicator may include a grip region. In some variations, the channel of the inner cannula includes a first and a second groove, so that the stiff member fits within the first groove and the implant fits within the second groove. The stiff member can be configured to rotate within the first groove of the channel to engage the implant within the second groove.

The engagement region of the applicator may be configured as a toothed region (e.g., having "teeth") for engaging at least some of the segments of the implant. The applicator may also include an external cannula located at the distal end of the applicator, and configured so that an implant within the inner cannula may pass through a channel in the external cannula. The external cannula can project to the site in the body for application of the implant.

Also described herein is a method of delivering an implant into a target site within a body. The method may include the steps of loading an implant into an applicator (wherein the applicator comprises an inner cannula having a channel configured to hold at least a portion of the implant and a stiff member within a channel of the inner cannula having a releasable engagement region configured to engage at least a portion of the implant), placing the distal portion of the applicator near the target site, and advancing the implant from the applicator into the target site.

In some variations, the step of advancing the implant includes engaging the engagement region of the stiff member with the implant and sliding the stiff member distally. The step of engaging the implant with the stiff member may involve rotating the stiff member axially within the applicator. Thus, the applicator can advance the implant distally or retract it proximally to adjust the position. In some variations, the method may include the steps of disengaging the engagement region of the stiff member from the implant, sliding the stiff member proximally, engaging the engagement region of the stiff member with the implant, and sliding the stiff member distally.

The method may also include the step of cutting the implant.

In some variations, the method may include the step of withdrawing the implant from the target site. For example, the implant may be withdrawn by engaging the engagement region of the stiff member with the implant and sliding the stiff member proximally.

Also described herein are locking devices for securing within non-soft body tissue. A locking device may include an elongate threaded body having a distal end and a proximal end, and at least one implant coupled near the distal end of the threaded body, wherein the implant comprises an array of flexibly connected segments. The elongate threaded body of the locking device may be configured as a bone screw. As used herein, and locking device may also include an anchoring device. In some variations, the device includes more than one implant coupled near the distal end of the threaded body.

The locking device may include a loop that is connected to the implant, and couples with the locking device (e.g., by fitting over the distal end of the locking device). In some variations, the implant extends proximally from the distal end of the device. The segments of the implant may be configured to couple with the threads of the threaded body to secure the device within a non-soft body tissue.

Also described herein are anchors for securing a fastener within a body comprising a plurality of flexibly connected segments and a coupler attached to the flexibly connected segments, wherein the coupler is configured to attach to a region of the fastener so that the flexibly connected segments will abut the fastener when the fastener is inserted within the body. The coupler may be a hook, loop, or other attachment for holding the implant to a fastener. In some variations, the coupler is a loop that is configured to fit over a screw (e.g., a bone screw).

Also described herein are methods of securing an implant within a body. The method may include inserting a locking device coupled to at least one implant into the body (wherein the implant comprises a plurality of flexibly connected segments), and fastening the locking device by engaging the implant between at least a portion of the locking device and the side of a cavity within the body. In some variations, the step of fastening comprises screwing the locking device into the body tissue (e.g., bone).

BRIEF DESCRIPTION OF THE DRAWINGS

Embodiments or variations are now described by way of example with reference to the accompanying drawings.

FIGS. 2A to 2F show variations of the described implant;

FIGS. 3A to 3E, 3G, 3I to 3N, 3P to 3T show variations of the described implant;

FIGS. 3F, 3H, 3W and 3X illustrate variations of interlocking segments of the described implant;

FIGS. 7A and 7B show one variation of an applicator driver;

FIG. 7C shows another variation of an applicator driver;

FIG. 7D shows the relationship between an applicator and variations of the driver;

FIG. 9B is a schematic cross-section of the screw closure shown in FIG. 9A taken along the longitudinal plane A-A.

FIG. 11 shows a hybrid ram applicator as described herein.

DETAILED DESCRIPTION

Figure 1A:
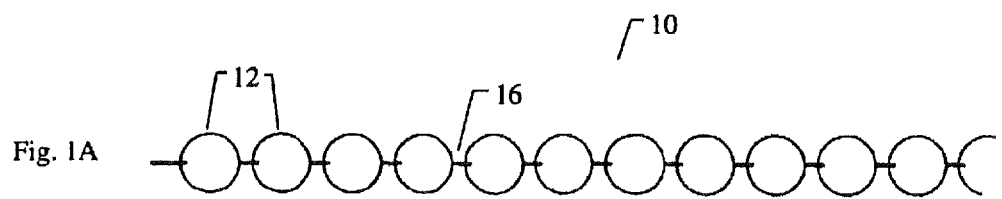
FIGS. 1A to 1E show variations of the described implant.
Figure 1B:
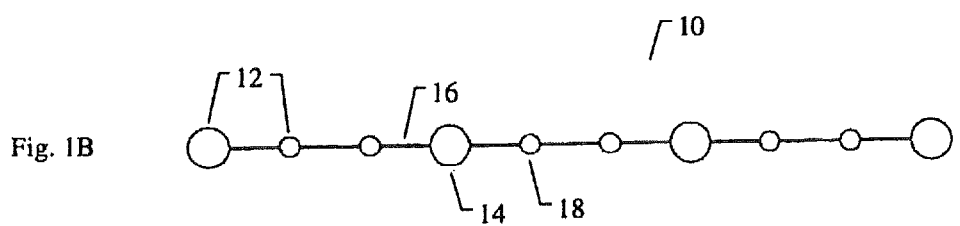

In the drawings, reference numeral 10 generally denotes an exemplary embodiment of a segmented implant for distracting, filling, creating, or maintaining a cavity in a tissue. The implant, applicator, locking devices (e.g., fixation screws and anchors), and methods of use may be used for distracting, supporting, filling, creating and maintaining the size of virtually any tissue cavity, particularly hard tissue cavities, including but not limited to: bone separations, fractures (including compression fractures), non-unions, removed tumors, removed cysts, in conjunction with joint replacement implants, and certain fusion procedures. Although example of implants, implant applicators, combinations of implants and applicators and methods of using the implants are described in the context of treating a vertebral compression fracture, the devices and methods of use described are not intended to be limited to vertebral compression fractures.

The implants, applicators and methods described herein are particularly relevant to insertion into body regions such as non-soft tissue cavities. Non-soft tissue cavities include hard tissues cavities such as cavities or voids such as bones, as well as cartilage, and bone connected to ligament and/or muscle, scar tissues, and other mineralized (e.g. calcified) tissues. Non-soft tissue cavities also include tissues cavities having at least one hard surface, including tissues having mixed compositions. For example, non-soft tissue cavities include cavities abutting bone, or cavities surrounded by bone, such as cavities within the spinal disk space, cavities within the bone marrow, and cavities adjacent to bone or bone and ligament.

FIGS. 1A to 1E illustrate variations of implants for distracting or filling a tissue cavity. The implant 10 in each of FIGS. 1A to 1E includes a plurality of segments (illustrated as pellets) that are flexibly joined. Segments of the segmented implants may include one or more pellets. A perspective view of an implant is shown in FIG. 1A. The segments 12 are shown as spherical pellets that are connected by a centrally located wire, string, or fiber 16. The joined pellets form a connected construct seen as a flexible linear array that may be inserted into a cavity to distract the cavity walls, to fill the cavity, or to provide continuing support to the cavity. As used herein, unless the context makes clear otherwise, "distract" or "distracting" refers to the process of separating (or enlarging) the walls of a cavity, particularly a bone cavity.

Crush Strength

An implant may be used to distract, to fill, to create or to maintain the size or shape of a hard tissue body cavity such as a bone cavity. In one variation, the described implant's segments 12 have crush strength adequate to withstand the forces required to distract and support the cavity without substantial compression or breaking of the segments. Crush strength is defined as average crush load per unit cross-sectional area at which the structure will break or crack, and may be expressed in pounds per square inch or megaPascals (MPa). Of course, the shape of a segment has both individual and group effects upon the crush strength of the implant after installation. The crush strength of an individual segment pellet, however, is a consideration for distracting a cavity. For roughly spherical pellets, force can be approximated as acting at discrete points on the surface of the sphere, so crush force may be approximated as the total force applied to crack the sphere. One factor effecting crush strength is compressible strength of the material.

Compressibility

It may be beneficial that the segments comprise any solid material having an appropriate compressible strength so that the implant assemblage is able to distract, fill and support a tissue cavity without substantially deforming. The segments preferably comprise biocompatible solids with high compressive strength. Compressibility and incompressibility generally describe the ability of molecules in a solid to be compacted or compressed (made more dense) under an applied force and/or their ability to return to their original density after removing the applied force. Compressibility of a solid may also be quantified by the bulk modulus of the substance (bulk modulus is the inverse of compressibility, and is the change in volume of a solid substance as the pressure on it is changed). A relatively incompressible material will have a higher bulk modulus than a more compressible material.

The compressive strength of cortical bone is approximately 166 MPa, and the compressive strength of cancellous (spongy) bone is approximately 4 MPa. In one variation, the implant should have a compressive strength of greater than approximately 20 MPa. In one variation, the implant should have a compressive strength less than cortical bone. In one variation, the implant has a compressive strength between about 20 and about 160 MPa. In one variation, the implant has a compressive strength between about 91 and about 160 MPa. In one variation, the implant has a compressive strength between about 100 and about 160 MPa. As a reference, the compressive strength of calcium sulfate is approximately 11 MPa.

The implant or segments of the implant may also have a mixed compressibility or crush strength, because a portion of the implant may be more compressible than another portion of the implant. For example, the implant may have a layer or coating of elastic or other compressible material. In some variations, the different segments may have different compressibilities. For example the coating may be add or otherwise alter the compression strength, an therefore the crush strength.

Segment Materials

The crush strength of the implant depends to a large extent, on the segment crush strength, which is a function of the composition, and to a lesser degree, the shape of the segment.

Materials with appropriate crush strength include, but are not limited to, metals, alloys, ceramics, certain inorganic oxides and phosphates, polymers, bone derived material, and combinations of these materials. The following descriptions of segment materials represent variations of the implant, and are not intended to limit the scope of the implant or segment materials. The implant segment may comprise, consist of, or consist essentially of the materials identified herein.

Bioabsorbable (or bioerodible) and non-bioabsorbable (or non-bioerodible) material may be used in the implant separately or in combination. Typically, the non-absorbable (or non-bioerodible) materials noted elsewhere provide segments and implants exhibiting a sustainable crush strength adequate to maintain the distraction of the cavity surfaces (e.g. bone cavity surfaces) over a long period of time. On the other hand, bioabsorbable (or bioerodible) segments exhibit a reduction in crush strength over time, as the material is acted upon by the body. However, bioabsorbable materials may also permit substantial tissue in-growth, allowing tissue to replace implant material while maintaining the distraction and supporting the filled cavity. In applications in which the likelihood of tissue re-growth is small, for example osteoporotic repair, a nonabsorbable implant may be desirable. Materials that are too rapidly bioabsorbed (for example, calcium sulfate hemihydrate) are generally inappropriate as segment materials, because they do not maintain the cavity structure and/or distraction.

Metals that may be used as segment materials include, but are not limited to, biocompatible metals and alloys, such as stainless steels, gold, silver, tantalum, cobalt chromium, titanium, platinum, rhodium, rhenium, ruthenium, and other alloys thereof, combinations thereof, or other equivalent materials.

Ceramic materials that may be used in the segments may include, but are not limited to, alumina, carbon or tricalcium phosphate or sintered masses or single crystals of hydroxyapatite. Ceramics capable of high crush strengths may be particularly relevant. Also useful are refractory metal and semi-metal oxides (tantalum oxides, aluminum oxides), phosphates (calcium phosphates), phosphides, borides (niobium borides, tungsten borides), carbides (aluminum carbides, boron carbides, niobium carbides, silicon carbides, tantalum carbides, titanium carbides, tungsten carbides, vanadium carbides, zirconium carbides), nitrides (boron nitrides, chromium nitrides, silicon nitrides, tantalum nitrides, titanium nitrides, zirconium nitrides), silicides (tantalum silicides, tungsten silicides, zirconium silicides), their mixtures, variously sintered as porous particulates or as solid formations.

Inorganic materials that may be used as segment materials include, but are not limited to, hardened glasses including oxides of silicon, sodium, calcium and phosphorous and combinations thereof.

Polymers that may be used as segment materials include, but are not limited to, elastomers (natural and synthetic rubbers, silicone rubbers), polymethyl methacrylate (PMMA), polyetheretherketone (PEEK), polymethymethacrylate (PMMA), polyglycolic acid and/or polylactic acid compounds, polyvinylchloride (PVC), polyethylene (PE, HDPE, UHMWPE, etc.), polystyrene (PS), polyesters (PET, polycaprolacton, polyglycolied, poylactide, poly-p-dixanone, poly-hydroxy-butylate), polyamides (Nylons, aromatic polyamides), polypropylene (PP), fluorocarbon polymers (PTFE, FTFCE, PVF, FEP) and other biocompatible materials. Other suitable polymers include: collagen and/or collagen derivative preparations alone or in combination with other biomaterials, chitin and chitosan preparations.

Bone derived materials that may be used as segment materials include, but are not limited to, bone autografts, bone allografts, bone xenografts, bone-derived tissue, bone-derived collagen, and the like.

Any combinations of these materials may be used as a segment material. Segments may include pellets of any of these materials, or combinations thereof. Finally, suitable known materials acceptable for use as hard tissue implant materials include various osteogenic and osteoinductive compositions, and combinations thereof. Certain glassy carbon forms are also quite useful.

Segment materials may also comprise radiopaque materials to enhance visualization of the implant, or the segments may incorporate a radiopaque material as a part of a segment (e.g., coatings, dispersed, or core materials). Examples of radiopaque materials include but are not limited to, barium sulfate, tungsten, bismuth compounds, tantalum, zirconium, platinum, gold, silver, stainless steel, titanium, alloys thereof, combinations thereof, or other equivalent materials for use as radiographic agents.

Coatings

Segments may include coatings to modify the surface properties of the segments, to have a biological effect, and/or to facilitate the insertion or removal of the implant. The coatings may be of any thickness. In one variation, the segment comprises layers of materials. In one variation, the segment has a hollow core.

In one variation of the implant described herein, a segment or segments may be coated with a therapeutic or medicinal material, such as an antibiotic. Additional medicinal materials may include, but are not limited to, anticoagulantsand bone-growth promoting agents. In one variation of the implant, the segments may be coated with a cross-linking or bonding compound that could facilitate adhesion either between the segments, with the body region, or both. In one variation the segments are coated with a cross-linker that can be activated after insertion into the bone cavity, for example, by adding an activating compound, by time delay, or by temperature. In one variation the segments are coated with a lubricant.

The segments may comprise one or more therapeutic or medicinal materials situated away from the surface, e.g., in pores within the segments.

Drug Delivery Using the Implant

The segments may also be embedded with one or more therapeutic or medicinal materials. For example, embedding the segments with an additional material may be particularly useful when the segment comprises a bioabsorbable (bioerodible) material. Thus, the segments may be used to deliver any drug or therapy. Drugs which are particularly useful may include, but are not limited to, growth factors and/or growth promoters (e.g. bone derived growth factors (BDGF), bone morphogenetic protein (BMP), etc.), antibacterials, antivirals, vascularizing agents, analgesics, anticoagulants, cell and/or gene therapies, etc.

In one variation an implant including a drug is inserted at or near a wound site. After an appropriate time the implant is removed. Thus, the implant may serve as a removable wound packing material. In one variation, the implant may be inserted with a removable drain. In one variation, the implant functions as a removable drain.

Any portion of the implant may be coated with, implanted with, embedded with, or made from a therapeutic or medicinal material, including but not limited to those described herein.

Flexible Joining Material

The implant segments may be connected in the implant as it is installed. The segments may be linked together in such a way that each segment in the implant is adjacent, perhaps directly adjacent or in contact with at least one other segment. Generally, each segment in the implant is adjacent, perhaps directly adjacent or in contact with at most two other segments. In some variations, the assembled segments form a linear array. In the variation of the implant shown in FIGS. 1A to 1E, the segments are linked in a linear array by attachment to a wire, filament, or string 16. The filament connecting the segments may comprise a separate, independent filament between each segment, or it may be a single continuous filament. The filament may comprise different materials, and may be different lengths. In one variation of the implant, the filament comprises one or more monofilaments. In another variation of the implant, the filament comprises one or more fibers. In a variation of the implant, the filament comprises one or more wires. The filament may comprise a bioabsorbable material. The filament may be rapidly bioabsorbable because (unlike the segments) the filament is not typically load bearing in supporting the cavity.

In one variation, the implant segments are connected in any way allowing sufficient flexibility to the resulting implant construct so that it may be introduced into a cavity such as a bone hollow. In one variation, the implant segments are flexibly connected so that a segment may contact another segment upon being implanted into a body region such as a bone hollow.

The connection material may comprise, for instance, a string, fiber or wire, variously of single or multiple strands. The connecting string or fiber may be flexible and allow the segments to be inserted into the treatment site. Suitable filament materials include virtually any biocompatible material, including but not limited to: natural materials (e.g. cottons, silks, collagen, etc), rubbers (e.g. natural and synthetic rubbers), composite yarns (e.g. carbon fiber yarns, ceramic fibers, metallic fibers), polymers (e.g. polyethylene, polyester, polyolefine, polyethylene terephthalate, polytetrafluoroethylene, polysulfone, nylons, polylactic acids, polyglycolic acids, mixtures and copolymers of polylactic and polyglycolic acids (PGLA such as "Vicryl" from Ethicon and "Dexon" from Davis & Geck), polydioxanone, various Nylons, polypropylene, etc., and the like). Suture material (natural and synthetic materials) are examples of particularly appropriate materials.

In one variation, the segments are adapted to connect to the filament, string or wire, for example, by having holes (through which the flexible joining material is threaded), by having attachment sites (to which the flexible joining material could be tied or otherwise attached), or by having a track or groove (which mate to the flexible joining material). In one variation the segments are adherent to the string or filament by a glue, adhesive, or the like. In some variations, they segments may be attached by structural method such as crimping or swaging, or the like.

In one variation, the segments are connected by adhesives or glues, such as solvent- or catalyst-curable materials including Silicone glues, rubbery epoxies, and adhesives suitable for the materials forming the segments. In one variation the segments are connected only by adhesives or glues such as those mentioned above.

The joining material does not itself have to be flexible, so long as it allows flexibly joined segments of an implant to "flex." In one variation of the implant, the segments are linked together by a solid linker. The implant is made flexible by incorporating a joint (e.g. socket type joins) between the solid linker and the segment. Solid linkers may be composed of the same material as the segments. Solid linkers may be wires made of one or more filaments comprising suitably biocompatible metals or alloys, e.g., stainless steels or superelastic alloys.

The flexible joining material may comprise any suitable materials including but not limited to: polymers, (e.g., polyfluorocarbons such as the various Teflons (including PTFE and expanded PTFE—ePTFE such as is sold as GORETEX), polypropylene, polyethylene, polyoxymethylene, polycarbonate, polyesters (including polyamides such as the Nylons), polyphenylene oxide, and polyurethane) or elastomeric polymers (e.g. various Silicones, natural rubber, butadiene-styrene rubber, carboxylic butadiene-styrene, butadiene-acrylonitrile rubber, carboxylic butadiene-acrylonitrile rubber, chlorobutadiene rubber, polybutadiene rubber, silicone rubbers, and acrylate rubbers, perhaps vulcanized, and other elastomeric materials) or a composite material.

The material used to join the segments may also have additional biological or mechanical properties. For example, the material may incorporate a therapeutic or medicinal agent for release (e.g., timed release). Examples of therapeutic agents include, but are not limited to, antibiotics, analgesics, anticoagulants, bone growth enhancing agents, cells or gene therapies, etc. The material may also incorporate other agents and materials, for example, radiopaque materials to aid visualizing the implant.

The joining material may also be severable. It may be desirable to have implants of certain lengths (e.g. a certain number of segments). It may also be desirable to have implants that are continuous, and allow the user to select their length by removing or cutting the connection between any two segments. For example, the joining material may be severable by mechanical, thermal, chemical, or electrical means.

In one variation, the joining material is removable from some or all of the segments during or after insertion into the cavity.

Joining Material as Flexible Tube

Figure 1C:
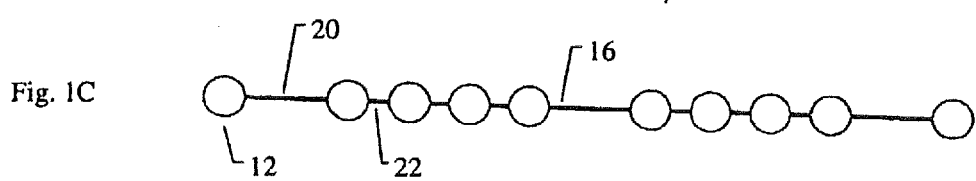
Figure 1D:
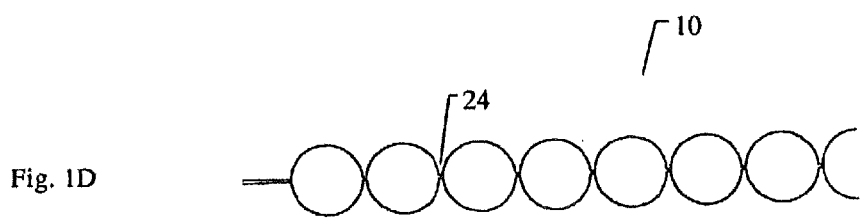
Figure 1E:
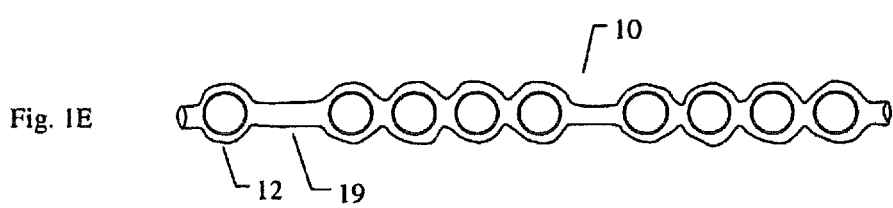

In the variation of the implant shown in FIG. 1E, the segments are linked together in linear array because they are held within a flexible tube 19. A flexible tube may be made of virtually any material, so long as the final implant is adequately flexible to allow bending of the implant. The flexible tube comprises a solid or continuous walled tube, a solid or continuous walled tube having openings in the wall, or a netting woven from string or fiber. The flexible tube may comprise one or more membrane, optionally made of an expandable or a stretchable material.

Figure 17A:
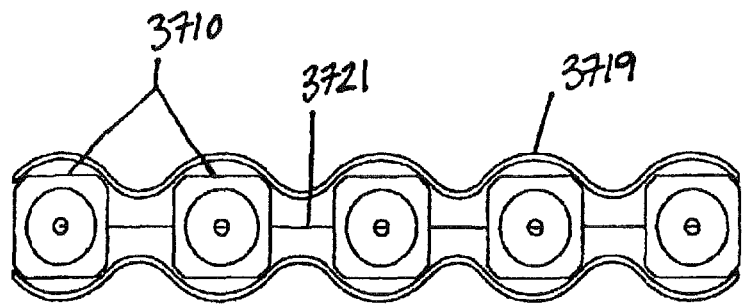
FIGS. 17A, 17B, and 17C show perspective views of the flexibly connected segments within flexible tubes instruments and implants described herein.

In one variation, the implant segments are linked by an expandable membrane. The expandable membrane material may be a fabric that has pores allowing passage of fluids and bone growth through it. For example, the membrane could be formed of a flexible polymeric fabric e.g., high molecular weight polyethylene. The flexible tube may be any material (e.g. woven, non-woven, extruded, etc) that is adequately flexible. In FIG. 17A, one variation of the implant has segments 3710 that are within the flexible tube 3719 that are also linked by a filament, wire, string, or other connecting or joining material 3721.

Figure 17B:
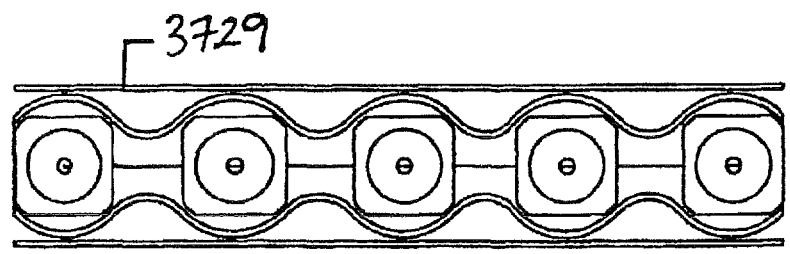

In one variation shown in FIG. 17B, the flexible tube with segments is located within a second flexible tube 3729. The internal flexible tube may contain perforations to allow the passage of fluids into the outer flexible tube. The internal flexible tube may contain variations that allow the passage of fluids into the outer flexible tube only after the implant is delivered into the non-soft tissue cavity. For example, an activating agent may make one or both of the flexible tubes porous (e.g., by adding a solvent such as water or other fluent material). In one variation, the passage of fluids between the flexible tubes (or from the flexible tube into adjacent body regions) occurs after compaction or after a specific geometry (e.g. bond angles) or position of the contained chain of segments is achieved. The inner flexible tube may be enclosed by any number (e.g., two or more) of flexible tubes.

Figure 17C:
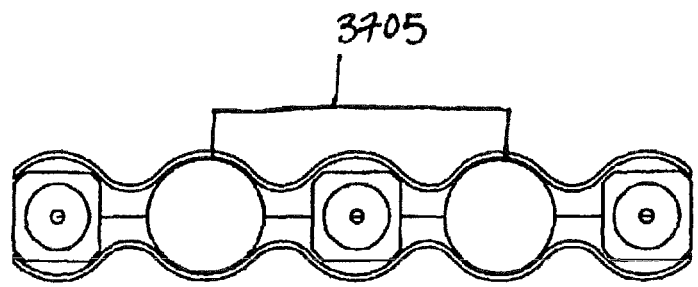

In one variation shown in FIG. 17C, fluent materials such as cements are contained within one or more segments within the flexible tube 3705. These specialized segments might be a crushable material that allows the release of the fluent material (such as a cement) into the flexible tube that can then interact with a secondary hardening catalyst located within the tube and react to begin setting to form a hardened final composite. This process would allow the settable material to harden within the tube after desired placement and packing of the flexible tube implant. In one variation, the flexible tube membrane might be permeable, allowing some of the hardenable, fluent, settable material to move to the external space surrounding the flexible tube. In one variation, the flexible tube would be impervious to the fluent material (e.g., no porous) and the cement would remain fully contained within the flexible tube.

Figure 18A:
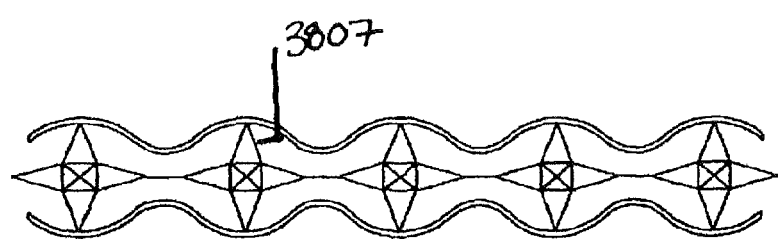
FIGS. 18A and 18B show perspective views of segments with sharp protusions contained within the flexible tube instrument and implant of FIG. 17B.
Figure 18B:
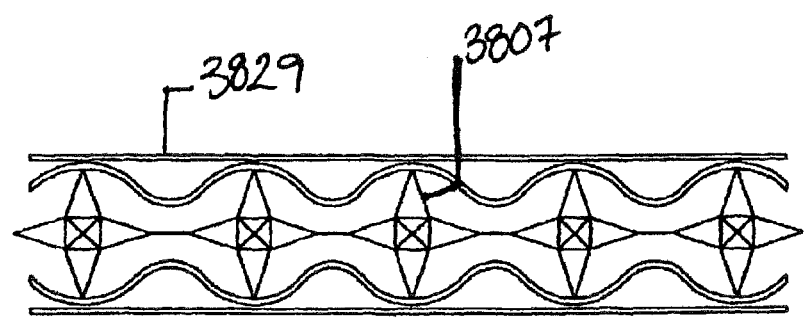

In one variation shown in FIG. 18A, the segments within the flexible tube may include sharp protrusions 3807 that allow the perforation of the flexible tube during or after delivery of the implant. This would allow the two fluent settling materials to mix and begin the hardening process after or during delivery of the implant In the variation shown in FIG. 17B, the flexible tube includes some segments with sharp protrusions and is contained within a second outer flexible tube 3829 that could contain a settling material released from the internal flexible tube. The sharp edges or protrusions may be caused to pierce the inner tube (and possibly the outer tube) in a controlled manner (e.g., by compaction).

In one variation, the flexible tube might be coated with a bonding agent. The bonding agent may allow adhesion of the implant to bone or other non-soft tissue within the cavity. The bonding agent may allow adhesion of the implanted flexible tube to itself. The bonding agent may allow adhesion to both. The bonding agent might be coated onto flexibly connected segments that are not contained within a flexible tube.

In one variation, two or more flexible tubes may be delivered simultaneously from within one delivery cannula. In one variation two or more chains of flexibly connected segments may be delivered simultaneously within one flexible tube. In one variation, two or more chains of flexibly connected segments, each individually enclosed within a flexible tube, may be contained within one outer flexible tube and may be delivered simultaneously within a delivery cannula. The segments contained within the flexible tube or tubes may be non-connected except by the flexible tube. In one variation two or more chains of segments may delivered without a flexible tube within one delivery cannula.

Figure 19A:
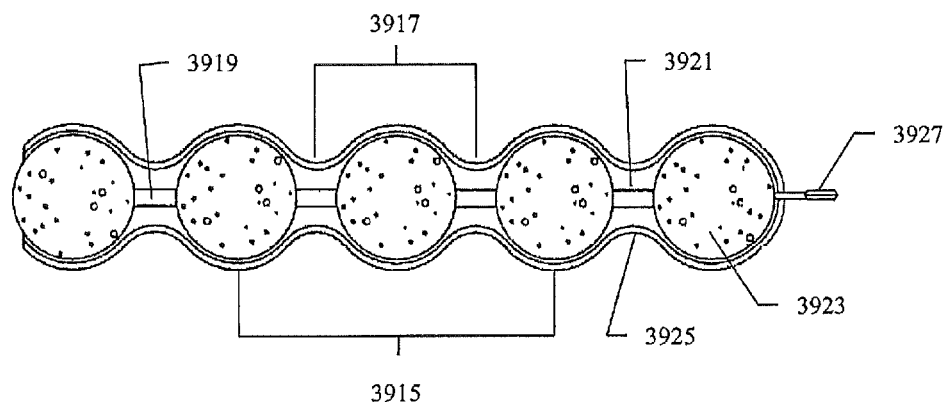
FIGS. 19A, 19B and 19C show perspective views of crushable and pervious segments within the flexible tube and implant of FIG. 17B.
Figure 20A:
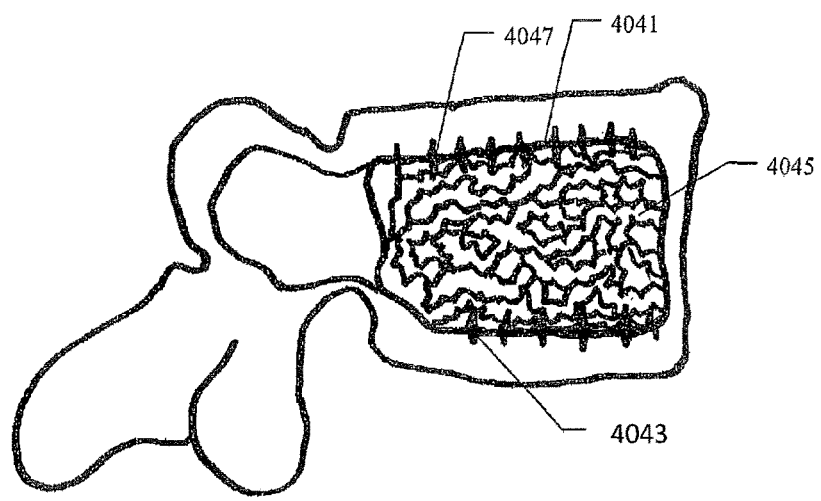
FIG. 20A shows a perspective view of single chains of segments at the top and bottom of a cavity with the space in between the chains containing the flexible tubes and implants of FIGS. 17A and 17B.
Figure 20B:
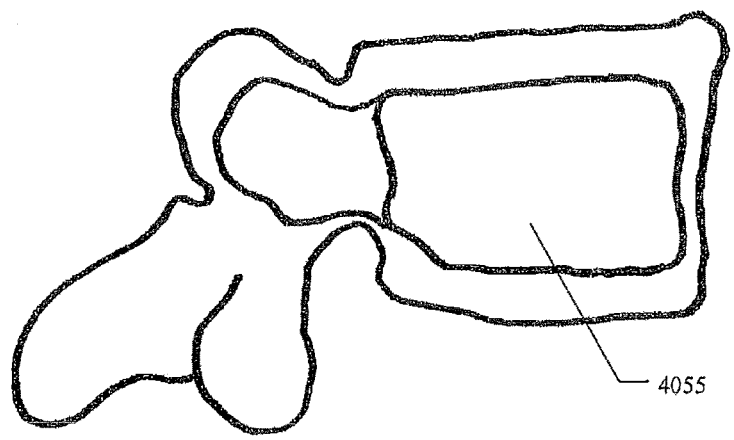
FIG. 20B shows a perspective of a vertebral cavity containing a UV hardened settable material.

The implants described herein may also include one or more transmission pathways for transmitting electromagnetic energy (e.g., light such as UV light, electrical or magnetic energy, etc.). This electromagnetic energy may be used to activate a fluent material within the implant (or adjacent to the implant), causing it to harden. For example, in one variation (as shown in FIG. 19A), the flexible tube contains electromagnetically transparent segments 3923 and connectors comprising a material that transfers electromagnetic energy (such as a fiber optic material 3921). Other types of electromagnetic energy that might be utilized could include gamma rays, infrared, x-rays or ultraviolet waves. In one example, the segments and connecting material can be surrounded by a fluent, UV-curing, settable material 3925, such as an epoxy, resins, polymer, monomer, or an acrylic, that is capable of being hardened upon exposure to an electromagnetic energy transferred through the connecting material, such as a fiber optic 3927. Examples of UV-curing materials include UV curable adhesive & potting compounds such as UV Cure 60-7155 (a one-component modified epoxy) and DYMAX UV resins. The use of UV-curing materials can control when the hardening of the settable material begins, providing additional control of delivery of the implant. The transparent segments might be composed of a polymer or any material that is capable of transferring light. The UV-curing material might be utilized in any cavity space where a controlled timing of delivery of a settable material is desired. For example the cavity might be a intra-vertebral space such as is shown in FIG. 20B. In one variation, the electromagnetic energy can be transferred through the sheath itself, which could be composed of a material capable of conducting the electromagnetic energy. Any appropriate transmission pathway may be used, including dedicated pathways (e.g., fiber optics, conductive wires, etc.) or pathways made of the segments and/or connecting filaments, the tube, or even the fluent material itself. In one variation, the segments within the flexible tube are coated with a material that can have a phase change when catalyzed by an electromagnetic energy. In one variation, a fluent or coating material may be catalyzed to harden (phase change) or become adhesive by the application of heat from a heat source (e.g., laser, electrical resistance, etc.). In one variation, the transfer of energy within the implant might be guided by making transfer from the implant, or in certain regions of the implant, inefficient. For example, some of the surfaces of the implant (e.g., within the tube or the segments) may include a surface finish treatment or coating to reflect or inhibit electromagnetic energy, distributing the energy within the implant in a predictable way.

Figure 19B:
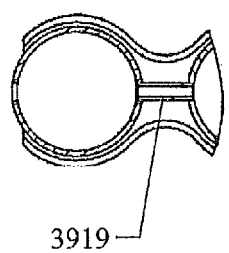
Figure 19C:
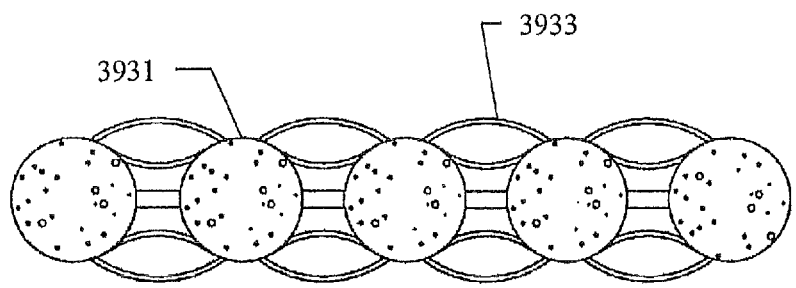

In one variation, an inner flexible tube contains segments and a fluent settable material (such as cement) and an outer flexible tube surrounds the inner flexible tube. The space surrounding the inner flexible tube contained within the outer flexible tube might contain a biologic bone growth material such as bone morphogenic protein. In one variation, the inner flexible tube is porous. In one variation the inner flexible tube is not porous (e.g., impervious to the passage of fluent material such as activatable cement). In the variation shown in FIG. 19A, the flexible tube contains porous regions. The flexible tube might be porous at the point of contact with the segments contained within the tube 3915 but not-porous along the rest of the tube 3917. As shown by FIG. 19B the segments might be connected within the flexible tube by small tubing 3919 that allows the passage of fluent materials between the segments. In one variation the flexible tube might be completely porous. In one variation shown in 19C the connecting member may be composed of one or more flexible tubes between the segments 3933 allowing a portion of the segment to be exposed directly to the cavity space such as a vertebral space 3931.

Multiple implants (e.g., including implants with different properties) may be used in the same procedure. In one variation shown in FIG. 20A a single chain of flexibly connected segments is placed along the top of a non-soft tissue cavity 4041 such as a vertebral space and one chain of flexibly connected segments across the bottom of the tissue cavity 4043. An implant of flexibly connected segments contained within a flexible tube may then be delivered into the cavity between the two individual chains 4045. In one variation, the individual segment chains are shaped in a manner that would cause them to penetrate the non-soft tissue 4047 such as bone endplates within a vertebra space resulting in the chains becoming secured.

In some variations, more than one linear arrays of implants may be used within the same flexible tube. For example, two or more linear arrays of implants may be combined (e.g., into a two or three dimensional array) within a flexible tube. Multiple linear arrays of implants may be twisted, intertwined, or braided together within a flexible tube to form an implant.

In one variation, the flexible tube contains segments and is designed to create a void within a non-soft tissue cavity. In one variation, the non-soft tissue is bone tissue. In one variation, the tissue is cancellous bone tissue. The flexible tube may be removed after the void is created.

In one variation, a flexible tube containing segments is delivered into a cavity such as a vertebral space to create a void within the space, and is then removed. A small amount of fluent adhesive material (such as cement) is applied to internal non-soft tissue such as the top and bottom bony endplates within a vertebra. A subsequent implant of flexibly connected segments contained within one or more flexible tubes is then delivered into the cavity. This implant may include a fluent settable material such as cement along with the segments within the flexible tube at the time of delivery into a cavity such as a vertebral space. In one variation, the secondary flexible tube implant is delivered without a void being created in advance.

Segment Dimension

FIGS. 1A to 4D show different variations of the segments 12 compatible with the implant 10. In FIG. 1 the segments are all shown as spherical pellets. FIG. 1B shows that the pellet size may vary. FIG. 1C shows that the spacing of the segments on the joining material (shown as a filament 16) may vary. The lengths of the implant (e.g. number of pellets) may also vary. Larger 14 segments and smaller 18 segments are arranged in the linear array. Virtually any combination of segment sizes and shapes may be used in the implant. Varying the size as shown in FIG. 1B may change the manner that the implant "packs" within a bone cavity. For example, packing of different sized segments may allow different spacing between the segments, and therefore different opportunities for tissue in-growth into the implant, different structural properties, and different loading patterns of adjacent structures.

Segmented implants may be configured so that the implant is securely packed into the body region (e.g. non-soft tissue cavity). Size, shape, and spacing all contribute to the packability of the implant within the body region. For example, the same implant may have segments of different sizes, shapes and spacing in order to optimize packing. Additional factors such as the ability of one or more segments to move along the linear axis of the implant may also contribute to packing.

The size of the segments may be selected to optimize the insertion into the cavity and use of the implant applicator described below. Thus, the segments may describe a range of sizes suitable for use with an applicator and/or suitable for insertion into a bone cavity of given dimensions. In one variation the segments are between 1 to 40 mm in diameter. In one variation the segments are between 1 to 37 mm in diameter. In one variation the segments are between 1 and 10 mm in diameter. In one variation, the segments are between 1 and 6 mm in diameter. In one variation the segments are approximately 3 mm in diameter. In one variation the segment diameter is an average segment diameter. In one variation, the segment diameter is the maximum diameter of a segment.

The implant may have different inter-segment spacing. FIG. 1C shows implant segments 12 arranged in a linear array in which there are larger 20 gaps and smaller 22 gaps between adjacent segments. Different arrangements of segments along the linear array may also have desirable effects on the packing behavior of the implant and the severability of the implant. FIG. 1D shows a variation of the implant in which the spacing between segments is extremely small 24, potentially reducing the flexibility of the implant. However, implant flexibility may also be increased by using more elastic joining materials and potentially allow greater packing.

The segments may also be slideable (or partially slideable) in one (e.g. the long or linear) axis of the implant. In one variation of the implant some of the segments are slideable and some of the segments are fixed to the joining material. In at least one variation of the implant, the slideable segments allow the implant to be "tensioned" by tightening the joining material, tending to stiffen the implant, perhaps to aid in anchoring the implant or distracting a bone separation, or in anchoring another implant or device.

The segments of the implant may also have different shapes, allowing different packing and implantation properties. FIG. 2 shows examples of segments with different shapes. FIGS. 2A and 2B show a schematic and perspective view of cubic segment 202 shapes with rounded edges. The parallel faces of these segments 204 allow closer packing between adjacent segments. FIG. 2C is also an implant with cubic segments 206. FIG. 2D shows an implant with rect-angular-shaped segments 208. FIG. 2E shows an implant with cylindrical segments 210. FIG. 2F shows an implant with a slightly more complex segment shape having more than six faces. Virtually any shape that will allow the implant to fill a cavity to distract a cavity, create a cavity, and/or tighten or secure another implant, may be used. As used herein, unless the context makes it clear otherwise, "fill" means that the bone cavity is supported in three dimensions.

Some variations of the implant assemblage described herein describes space-filling implants (for filling, distracting, void creation, etc.). Thus, implant segments may be adapted specifically to fill three dimensional spaces.

The implant may have segments of different shapes, including shapes that are configured to communicate with each other, for example, to interlock. Several examples of interlocking shapes are shown in FIG. 3A to 3X. In FIG. 3A to 3G, the bullet-shaped 302 segments have a front end 306 and a back end 304, and at least some of them may slide along the axis of the linear array of the implant 10. The back end of one segment can engage with the front end of an adjacent segment as shown 310.

The segments may also be shaped to engage non-adjacent segments, for example, by having side faces that engage with other segments. The segments may also be shaped to engage with the walls of the cavity.

In FIG. 3E to 3G, the segments have a bullet shape with a conical nose 320, a cylindrical body 322, a conical recessed rear 324, with linear and rotational inner-locking features, 326. FIG. 3F shows a frontal view of two segments interlocked; FIGS. 3E and 3G show linked segments. The external surface has an advancing helical ramp 330 for assistance in advancement of a segment relative to adjacent segments when an axial load and rotational load are simultaneously applied to the implant. These features aid in compacting and elevating the hard tissue around the cavity being filled. The flexible rear extension 334 with external round 332 increase the likelihood of interstitial placement.

In FIGS. 3H to 3K, the implant comprises common segment shapes that have six over-lapping male spherical ball geometries creating a complex external multiply spherical surface 340. FIG. 3H shows three segments interacting. FIGS. 3I to 3K show linked segments. These segments may interlock because of the spheres nesting within the adjacent segments' depression created by the curved (e.g., semispherical) segment surfaces creating multiple coincident mating tangency points 342. The segments can be arranged along the connective member in a common entry and exit orientation 344 as in FIGS. 3I and 3K or an alternating pattern 346 as in FIG. 3J.

Figure 3L:
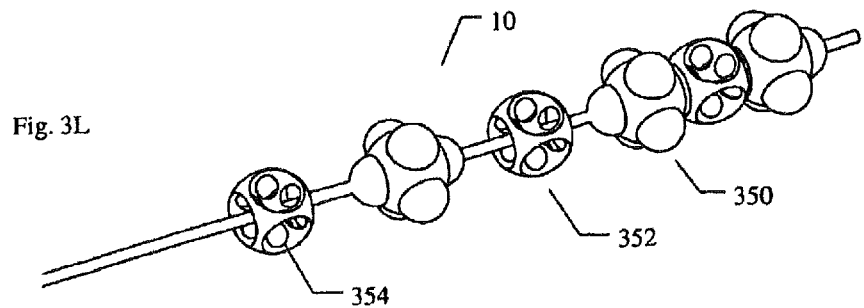
Figure 3M:
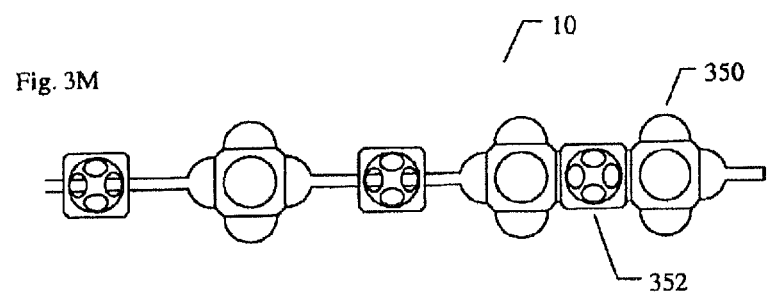

In FIGS. 3L and 3M, the implant 10 consists of two different segment shapes alternating and repeating along the connective member. The first segment 350 is similar to the segment described in FIGS. 3H to 3K consisting of six over-lapping male spherical ball geometries 340. The second segment 352 is a segment that has six female spherical recesses 354 that will enable tight interlocking and packing of the implant within the cavity.

Figure 3N:
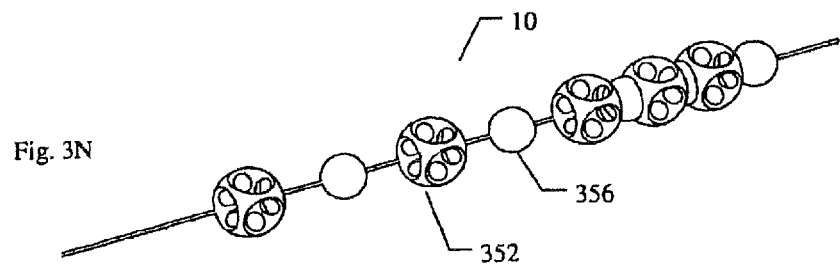
Figure 3P:
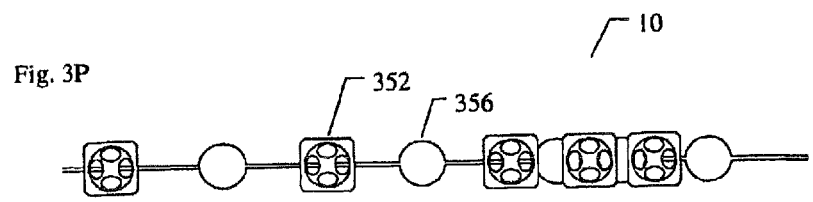

In FIGS. 3N and 3P the implant 10 consists of two different segment shapes alternating and repeating along the connective member. The first segment 352 is similar to the segment in FIGS. 3L and 3M. The second segment 356 is spherical. The configuration of this implant affords a tight packing with numerous mating receptacles open to accept the spherical segments and thus may be less dependent on packing order than other variations.

Figure 3Q:
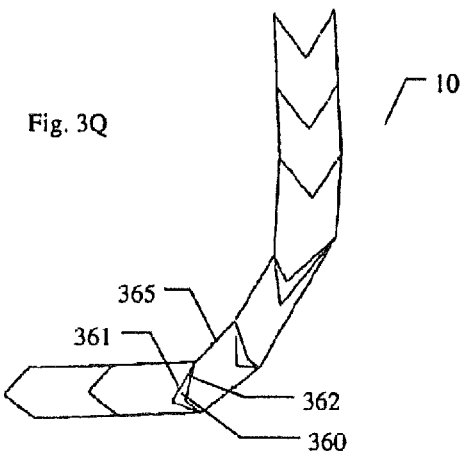

In FIG. 3Q, the implant 10 consists of two different segment shapes alternating and repeating along the connective member. The first segment 360 is arrowhead-shaped with front 361 and rear faces 362 pointed and made up of two angled faces. The second segment 365 is an elongated arrowhead with otherwise similar front and rear faces. The segments can be arranged in a manner that will allow a control of the desired mating and direction that the segments will follow once the segments leave the delivery cannula and meet resistance within the cavity. The direction change will be dictated by slight angular differences between the mating arrowheads.

Figure 3R:
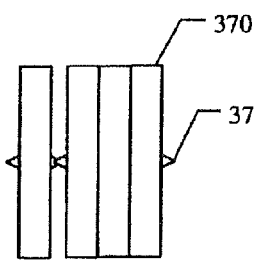
Figure 3S:
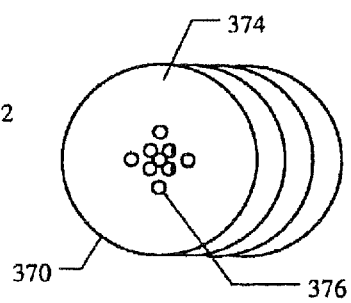
Figure 3T:
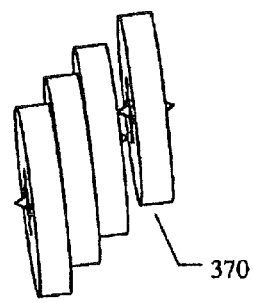

In FIG. 3R the implant comprises common segments shaped like coins 370 with conical spikes 372 protruding from the faces of the coins. The coin faces 374 have holes through them 376 that facilitates stacking of the coins, and the spikes are conically shaped to facilitate the self-centering stacking of the segments. The stacked coins create common tangency points 180 degrees opposed from each other that create two parallel planes of support.

Figure 3W:
Figure 3X:
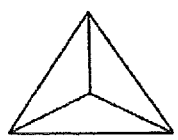

In FIG. 3W the segments have a cross-sectional area that is rectangular with various previously described front and rear geometries.

In FIG. 3X the segment cross-section is triangular with various previously described front and rear geometries. In some variations, the segments can have polygonal cross-sections, for example, hexagonal, octagonal, etc.

The aspect ratio of the segments' length relative to the segments' height and width can be varied in order to allow variations of stacking, packing, steering or elevating, depending on the desired result.

Figure 4A:
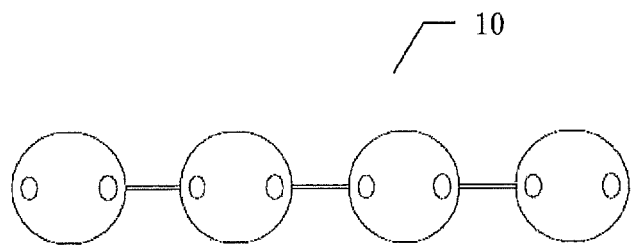
FIGS. 4A to 4D show variations of the described implant.
Figure 4B:
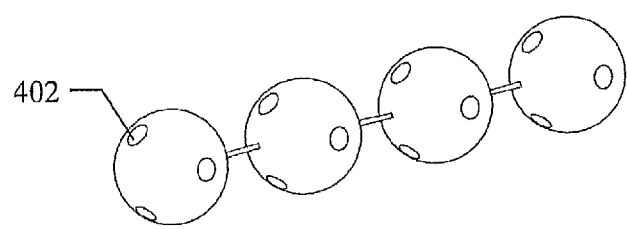
Figure 4C:
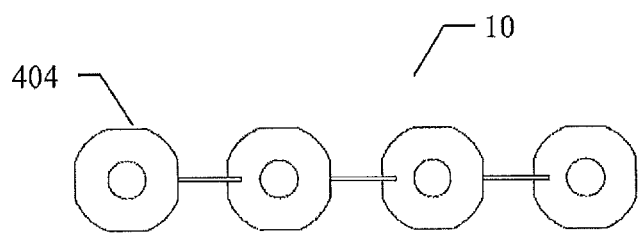
Figure 4D:
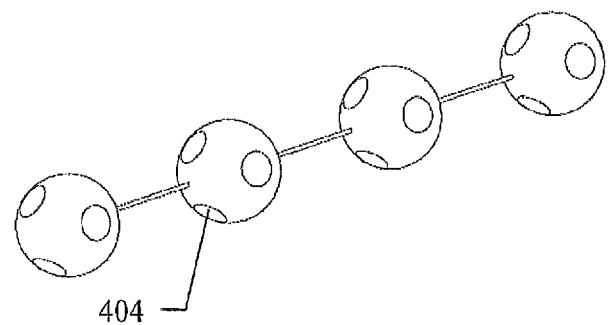

Many of the implant segments shown (e.g. FIGS. 1, 2 and 3A-3K and 3Q-3T) are illustrated as substantially 'solid.' Implant segments may also be hollow or have passages for either the joining material or additional material such as a fluent material (e.g. cement). Implant segments may also be porous, for example, to facilitate tissue in-growth, or reduce overall segment weight. FIGS. 4A and 4B show an implant that has passages 402. FIGS. 4C and 4D show an implant with pores, or hollow spaces, 404 that do not span the length of the segment. In one variation the pores 404 are dimples.

Implant segments may also be used with a fluent material. Examples of fluent materials include cements (e.g. bone cements, synthetic bone graft cements, etc.), therapeutics (e.g. bone morphogenic proteins, cells or gene therapies, bone growth factors), or combinations or substitutions thereof. In one variation the fluent material is applied into the cavity after the implant has been inserted. In one variation the fluent material is added before the implant. In one variation, the fluent material is added concurrent with insertion of the implant. In one variation the fluent material is inserted into the flexible joining material (e.g. a flexible tube around the implant segments). The flexible tube may be impermeable to the fluent material, keeping it substantially contained within the bone cavity.

Applicator

An applicator may be provided to insert a material such as the implant into a cavity to fill or distract the cavity, and/or to create or expand a cavity. The applicators described herein may be used to insert or remove an implant described herein. The applicators described herein may be used with any compatible material, including but not limited to individual pellets, fluent materials, and linear arrays of any materials desirable for insertion or removal from the body.

Figure 5:
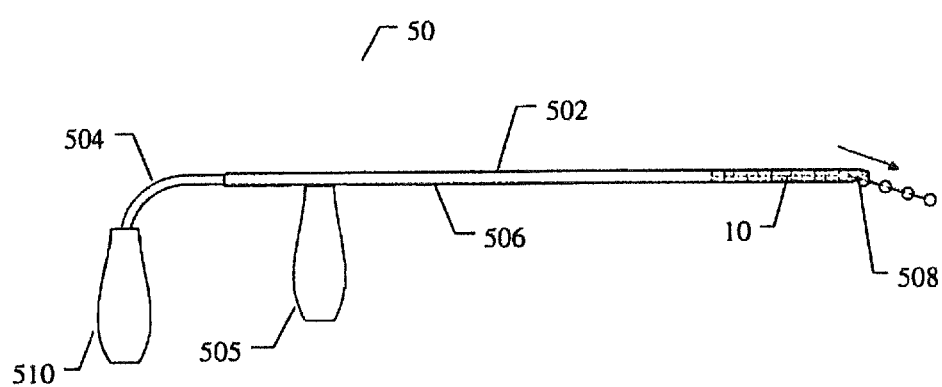
FIG. 5 illustrates a variation of an applicator for the implant.

FIG. 5 shows an applicator 50 useful for inserting an implant into a cavity (e.g. a bone cavity). The applicator has a cannula 502 having a distal and a proximal end and a lumen 506 with a handle 505 to aid in controlling the distal end orientation of the cannula. An implant 10 can be inserted into a bone cavity from the distal end of the cannula through an opening at the distal end 508. A feed guide 504 connects to the proximal end of the cannula. The feed guide can insert or withdraw the implant in and out of the lumen of the cannula through an opening in the proximal end of the cannula. An applicator may also have a handle 510 or a feed chamber to store implant material.

Cannula

The cannula may be an elongated tubular member having a lumen or passage to facilitate the movement of an implant through the cannula. The inner lumen of the cannula may be configured to hold and allow the passage of an implant. The inner surface of the lumen may be size-matched to the diameter of the implant. Alternatively, the size of the implant (e.g. segment size) may be limited by the inner diameter of the applicator cannula. The inner surface of the cannula may include a material that facilitates the movement of an implant (for example, a friction-reducing coating or a lubricant). The cannula may also allow the passage of a secondary filling material (e.g. a fluent material) before, after and/or during the insertion of an implant. An applicator cannula may be flexible or rigid.

The cannula may also have a fastener towards the distal end to hold the cannula in place on the outer surface of the bone being treated. A fastener or gripper near the distal end of the cannula may be used to aid the user in holding an applicator steady while inserting the implant to distract a bone cavity. In one variation the distal end of the cannula is threaded to facilitate insertion into, for example, the pedicle of a vertebra. The threads may further serve as a fastener or gripper.

The distal end of an applicator cannula may be adapted to aid in penetrating and/or distracting a bone cavity. In one variation, the distal end of the cannula includes a trocar. In one variation, the distal end of the cannula includes a spreader to separate bone surfaces and aid insertion of an implant.

Figure 6A:
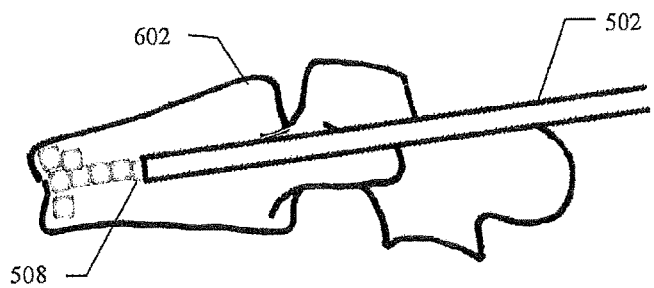
FIGS. 6A to 6C illustrate variations of the distal cannula tip of an applicator.

The distal opening of an applicator cannula may be located at the distal-most part of the cannula, or it may be located all or partly on the perpendicular axis of the cannula (e.g. on the side of the cannula, or at an angle), allowing more directional filling of a bone cavity by an applicator. FIG. 6A shows the distal end of an applicator cannula in which the distal opening is the extreme distal end of the cannula. The implant 10 exits the applicator 502 through the cannula's distal opening 508, and begins to fill the bone cavity 602, as shown.

Figure 6B:
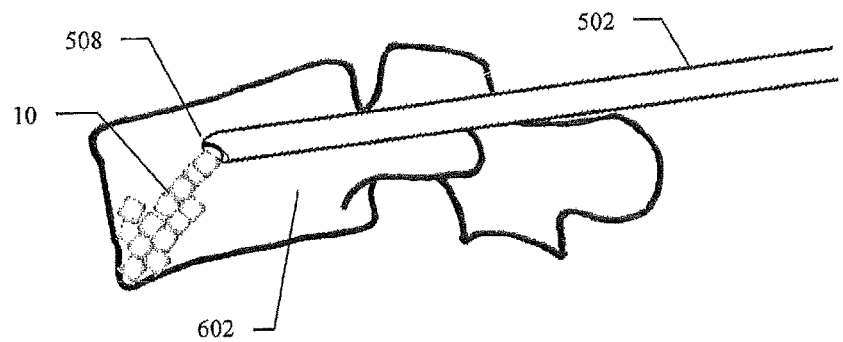
Figure 6C:
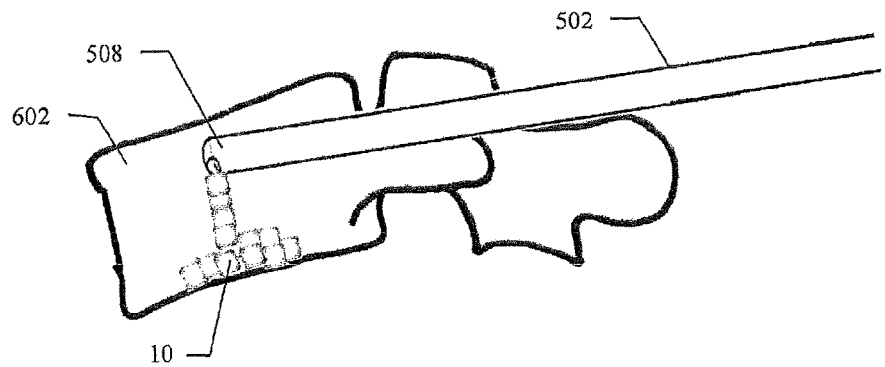

FIG. 6B shows the distal end of an applicator cannula in which the distal opening 508 is at a 45° angle from the long axis of the cannula. Thus the implant 10 is inserted into the bone cavity 602 at a 45° angle relative to the cannula. FIG. 6C shows the distal end of an applicator cannula in which the distal opening 508 is at a 90° angle from the long axis of the cannula. Thus the implant 10 is inserted into the bone cavity 602 perpendicular to the cannula.

The outer surface of the cannula may have graduated indicia that provide depth of penetration information during insertion by the user.

An applicator may be operated with a guide cannula. In one variation, an applicator cannula fits into the lumen of a guide cannula; the guide cannula is used to locate and prepare the bone cavity for insertion of the implant by an applicator. In one variation, an applicator cannula locks into a guide cannula and the guide cannula is secured to the bone that is being operated upon.

Figure 10:
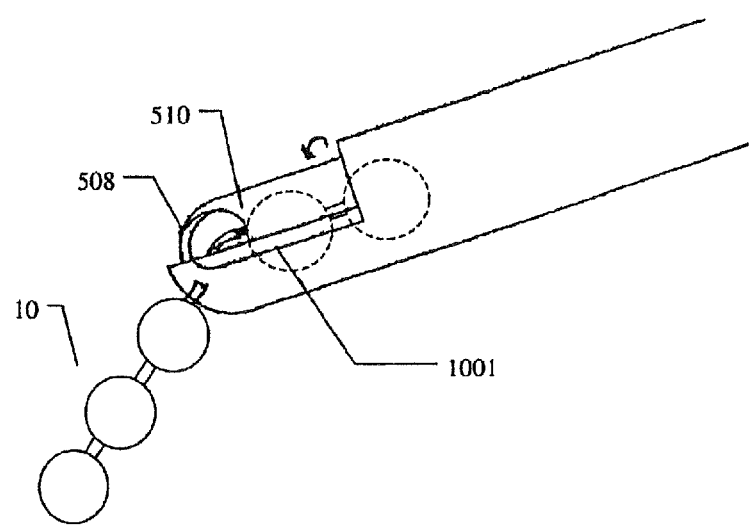
FIG. 10 shows a cutter for cutting segments of the implant as described herein.
Figure 12A:
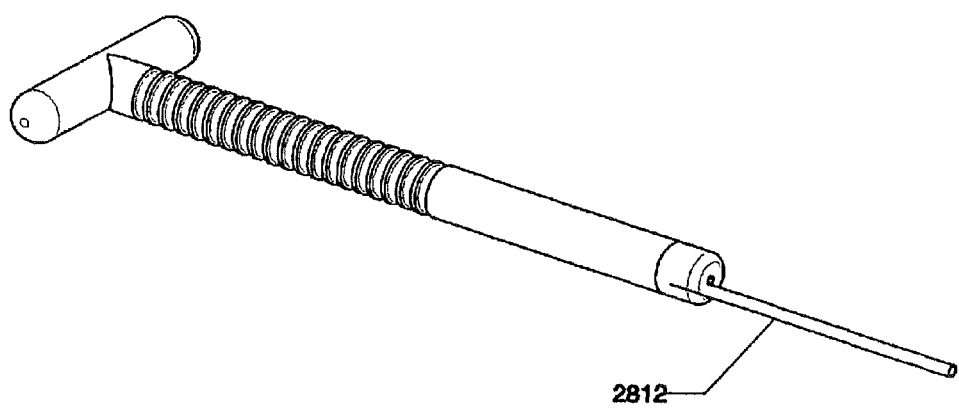
FIGS. 12A to 12D show components of the hybrid ram applicator of FIG. 11.
Figure 12B:
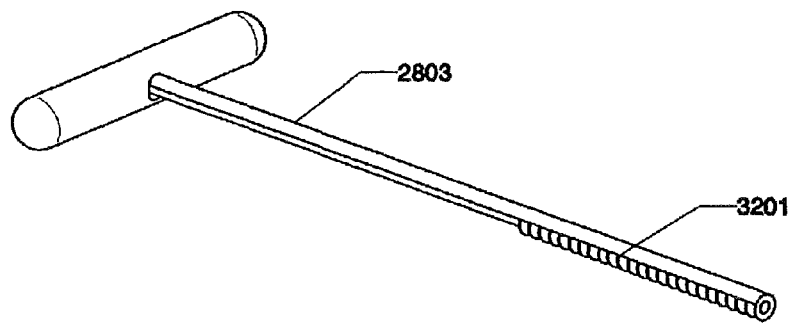
Figure 12C:
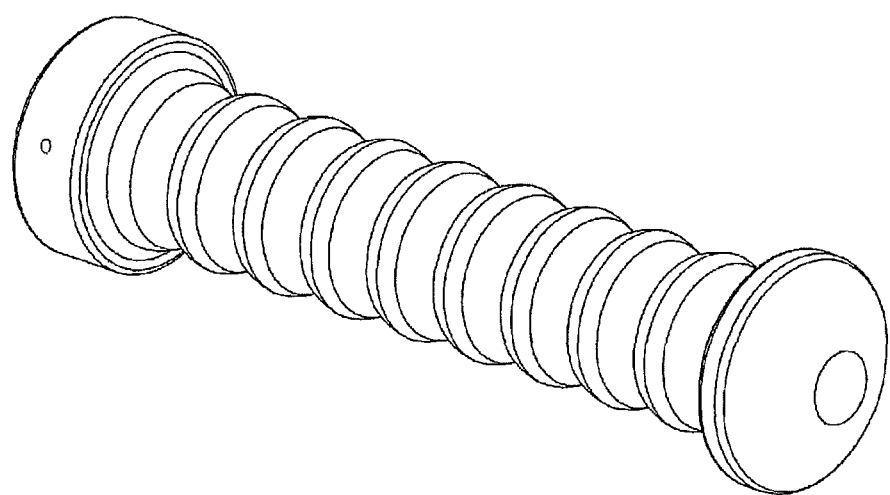
Figure 12D:
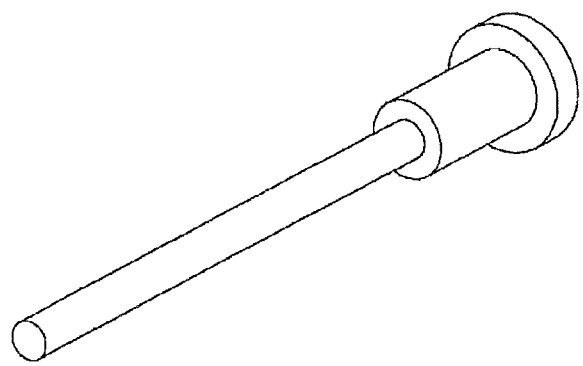
Figure 13A:
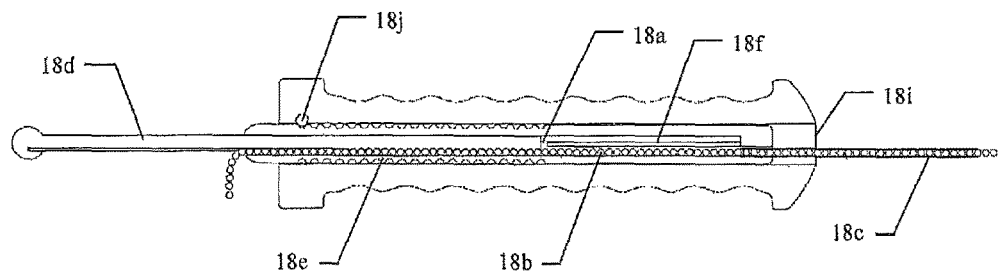
FIGS. 13A to 13C show cross-sections through the hybrid ram applicator of FIG. 11.
Figure 13B:
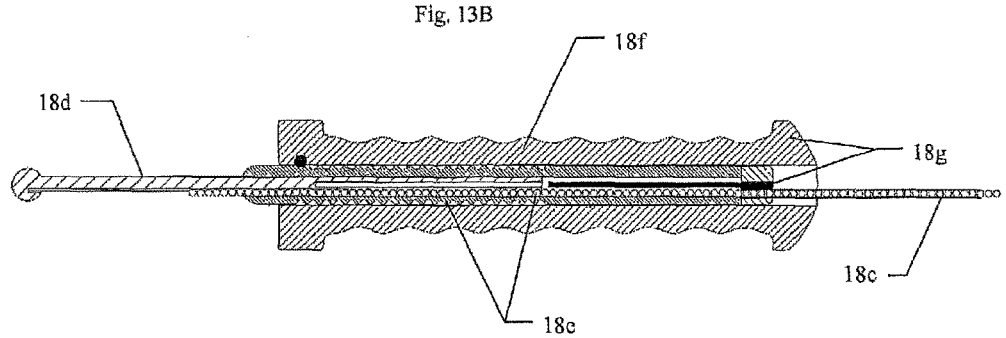
Figure 13C:
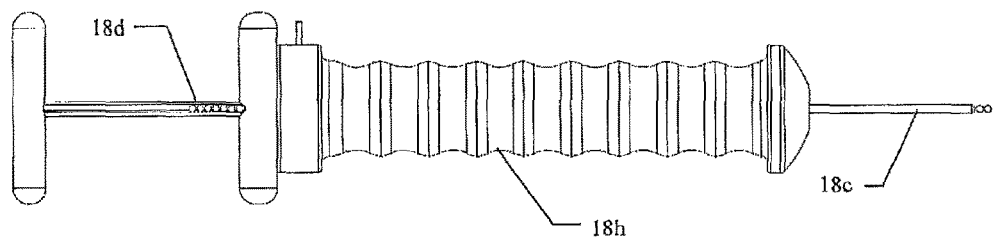
Figure 14A:
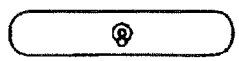
FIGS. 14A to 14C show perspective views of the internal cannula region of the hybrid ram applicator of FIG. 11.
Figure 14B:
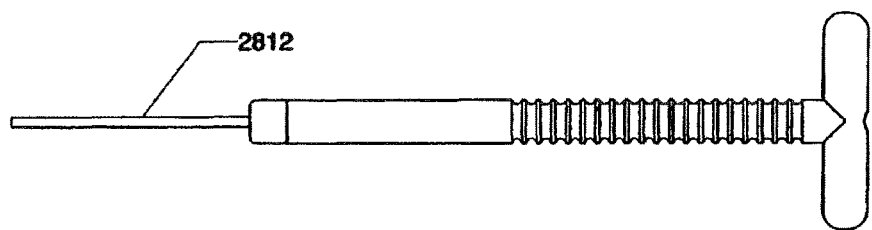
Figure 14C:
Figure 15A:
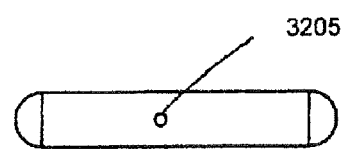
FIGS. 15A to 15B show perspective views of the reciprocating ram region of the hybrid ram applicator of FIG. 11.
Figure 15B:
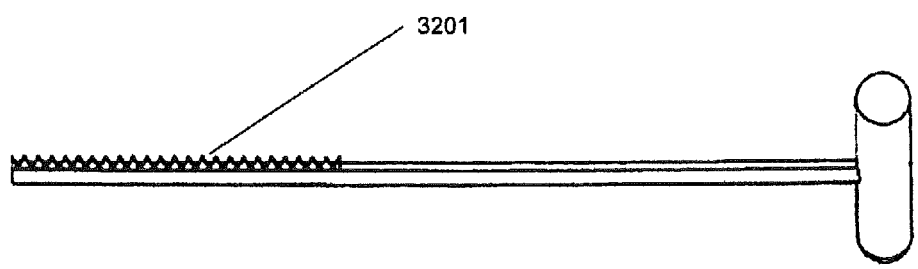
Figure 16A:
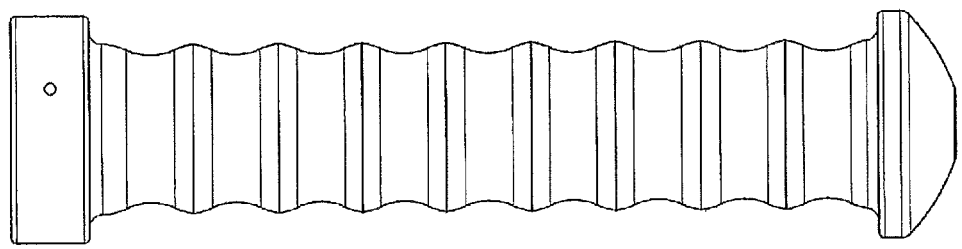
FIGS. 16A to 16C show perspective and cross-sectional views of the outer sheath region of the hybrid ram applicator of FIG. 11.
Figure 16B:
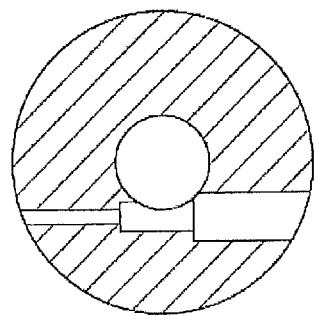
Figure 16C:
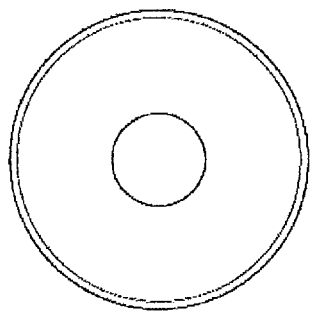

An applicator may also include a cutter configured to sever the implant by removing the connection between two of the segments in the linear array of an implant. An example of a cutter 1001 is shown in FIG. 10. The cutter may be located at least partly at the distal end of the cannula. The cutter may be located at least partly within a region of the inner lumen of the cannula. In one variation the cutter is located at an outer surface 509 of the distal end of an applicator cannula, adjacent to the distal opening 508. Rotating an external sheath drives a cutting edge across the cannula's distal opening thereby severing the connection between implant segments. In this variation the cutter is actuated by rotating the external sheath 510. As illustrated in FIG. 10, the cutter may be a mechanical cutter capable of applying force to sever the implant. Additional examples of mechanical cutters include but are not limited to, a blade, a scissor-like cutter, and the like. The cutter may be an electrical cutter capable of applying electrical energy to sever the implant. The cutter may be a chemical cutter capable of chemically severing the implant, for example, by applying a compound that reacts with the joining material of the implant. The cutter may be a thermal cutter which acts, for example, by heating the material connecting the segments causing it to release. The cutter may be any combination of mechanical, electrical, chemical and thermal cutter. The cutter may be controlled by a cutting controller. The cutting controller may be controlled directly by the user, or as part of a system.

Driver

An applicator may further comprise a driver for applying force to the implant in order to move the implant within the cannula to insert the implant into or withdraw the implant from a bone cavity. An applicator may be a mechanical drive (e.g. linear driver, a rotary driver, etc.), a pneumatic driver, hydraulic driver, a magnetic driver, an electric driver, or any combination thereof. Examples of drivers include, but are not limited to, rotating auger drivers, and rotating cog drivers. The driver is preferably a rotatable driver. Force generated by the driver is transferred to the implant (or a part of the implant), moving the implant within the cannula, in either the proximal or distal direction. In one variation, the driver is located at least partly within the cannula. In one variation the driver is located at least partly within the feed guide. An introducer member may comprise a driver as described here.

Applicator drivers engage at least a region of an implant. FIGS. 7A and 7B illustrate a cog driver 702 engaging at least part of an implant 10. As the cog is rotated about its central axis 708, in the direction indicated by the arrows (704 and 706), the implant is moved in the complimentary direction because segments of the implant 12 have engaged with the cog teeth 712 and are pulled or pushed in the direction of the rotation as shown. Because the segments of the implant are connected, movement of at least one of the segments results in moving the implant. An applicator driver may comprise more than one cog, or a cog and other driver components. FIGS. 7A and 7B also show the driver (a cog) at least partly in the lumen 506 of the applicator cannula 502.

In one variation, the cog is a friction wheel. In one variation, an outer surface of the friction wheel driver engages one or more regions of an implant (e.g. a segment). When the cog is a friction wheel, it may not have "teeth" which engage the implant.

FIG. 7C shows a rotating auger driver. In one variation, the auger is a continuously threaded rod 720; the implant's segments 12 fit within the threading gaps 722. In one variation, the rotating auger is located at least partly within the cannula. At least some of the implant segments are seated in the auger and are prevented from rotating around the long axis of the auger, for example by the geometry of the cannula or chamber surrounding the auger. Rotating the auger forces the segments (and thus the implant) to move down the long axis of the rod. Reversing the direction of rotation of the auger changes the direction that the implant moves. An applicator driver may comprise more than one auger, or an auger and other driver components.

A driver may also be at least partially within the cannula. In one embodiment the cannula lumen contains a rotatable auger. In one variation the driver is entirely located within the cannula.

A driver may be located at the proximal end of the applicator cannula, as indicated in FIG. 7D. Force applied by the driver moves an implant within the cannula, into or out of the bone cavity 602. The driver may be capable of moving an implant into or out of a non-soft cavity (e.g., bone cavity) by changing the direction that force is applied to the implant. An applicator driver may be attached to, integral to, or coupled to a feed guide.

Feed Guide

An applicator may include a feed guide 504 for loading the applicator cannula with an implant. A feed guide may be coupled to the proximal end of the cannula as shown in FIG. 5. A feed guide may comprise a chamber, a cartridge, a track, or other such structure in which an implant can be held. The feed guide may orient the implant for inserting or withdrawing from the cannula. The feed guide may also assist in engaging an implant with a driver.

In one variation, a feed guide is preloaded with an implant. For example, it may be advantageous to have the feed guide be a pre-loaded cartridge holding an implant. Such a feed guide may be separately sterilized and interchangeable between applicators.

In one variation, the feed guide includes a track configured to guide an implant. A track may keep the implant from jamming or tangling within the applicator. A track may further allow a long implant to be stored compactly. The feed guide may also help regulate the amount of force needed to move the implant.

In one variation the feed guide may be configured to engage an implant into a driver. In one variation a driver is at least partly contained within the feed guide. In one variation the feed guide attaches to a driver. In one variation the feed guide is configured as an opening in the cannula into which an implant may be manually inserted.

Controller

An applicator for inserting an implant may also include a controller for controlling the applicator driver. A controller may be manually or automatically operated. A controller may control the force applied by the driver. The controller may control the rate of insertion/withdrawal of an implant. A controller may control the direction that force is applied (e.g. forward/reverse). A controller may be operated by a user.

An applicator may also include detectors or indicators for registering implant and applicator parameters. In one variation an applicator includes a detector for determining and/or indicating the force applied by the applicator to insert or withdraw an implant. When a cavity is being filled, and particularly when a bone cavity is being distracted, an implant may be applied using a force adequate to insure that the implant is properly positioned within the cavity. Thus it may be important to monitor force and pressure applied to the implant or volume of implants, and/or the tissue. Feedback mechanisms may also be used to regulate the actions of the applicator, including the force applied by the applicator.

An applicator may also include detectors or indicators for indicating the status of the implant. For example, a sensor may indicate the amount of implant inserted, the amount of implant left in the applicator, and/or the position of the implant within the applicator or the bone cavity. In one variation, the applicator includes a force gauge for detecting the force applied by the applicator on the implant being inserted. The applicator may also include a display capable of indicating a status. Examples of the kinds of status that the display could indicate include, but are not limited to, force applied, total volume, linear feed rate, volume feed rate, amount of implant material inserted, and/or amount of implant material remaining in the applicator.

Implants Compatible with the Applicator

The application described herein may be used with any compatible implant, including but not limited to discrete (loose) pellets or segments of any material (including segments or pellets as described herein), fluent materials (e.g. cements, bone fillers, etc.), and any implant, particularly those comprising a linear array of elements. Such applicators may also be useful for filling and distracting bone cavities. In one variation the applicator comprises a cannula and a driver where the driver further comprises an auger or a cog. The auger or cog propels the discrete pellet, fluent material, or combination of implants, discrete pellets and/or fluent material, down the cannula in order to fill or distract the cavity into which the cannula has been inserted. It may be particularly advantageous to use the applicator with flexibly connected implants, including those described herein, because the applicator may be used to controllably insert and remove flexibly connected implants.

Additional exemplary applications of the applicator and/ or implants as described herein are given below. These examples are intended only to illustrate various embodiments of the implant, applicator, and methods of use, and are not intended to be in any way limiting.

EXAMPLES

In general, the implants and/or applicators described herein may be used to distract an existing body region. In one variation, the body region is a non-soft tissue cavity. In one variation, the body region is a hard tissue cavity, such as a bone cavity arising from a tumor, injury or surgery.

Figure 8A:
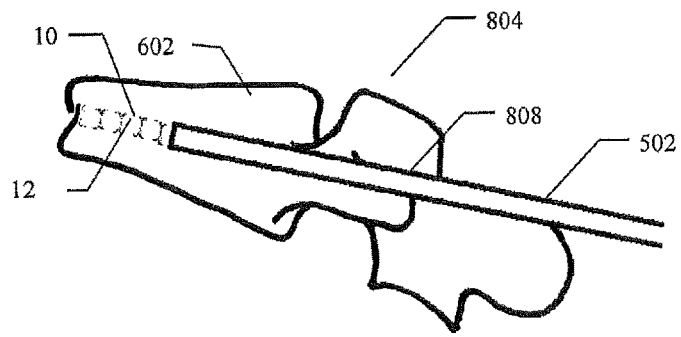
FIGS. 8A to 8C show insertion of an implant into a vertebral body.
Figure 8B:
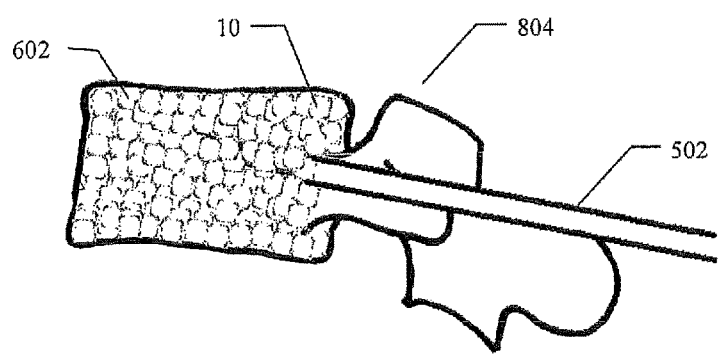
Figure 8C:
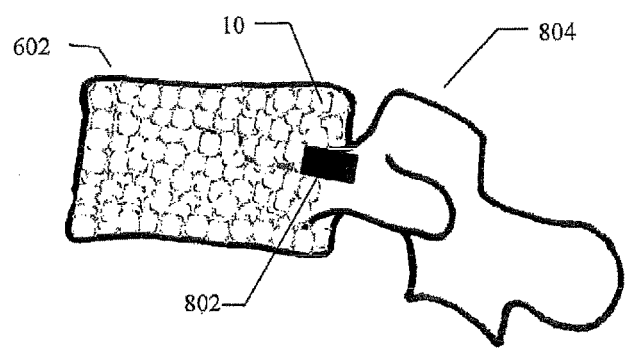

FIG. 8A to 8C shows an example of inserting an implant into a bone cavity 602. In this example, the bone cavity is part of a vertebral compression fracture. Other examples of bone disorders and fractures which may be distracted include, but are not limited to, tibial plateau fractures, femoral head necrosis, osteonecrosis of the hip, knee injury, etc. FIG. 8A shows an applicator 502 inserted into a vertebral compression fracture 804 through the vertebral pedicle 808 (in some variations, this could also be done through a transpedicular path, or otherwise); the applicator is inserting an implant 10 into the collapsed region. The implant is shown as a linear array of pellets 12. These segments of the implant may be continuously added to the bone cavity to first fill and pack within the cavity. Once the cavity is filled, adding further segments elevates the collapsed bone. FIG. 8B shows the bone cavity after it has been distracted by application of the implant. While some of the individual segments of the implant remain joined and connected to the applicator, the user may adjust the amount of distraction by removing and/or adding segments of the implant until the shape of the collapsed vertebra has been set to an optimal shape. In one variation, the optimal shape is the natural (uncompressed) position.

Compaction of the Implant within a Cavity

Once an implant is inserted, it may be compacted within the body cavity by packing the individual segments. Any appropriate device or method may be used to compact the implant segments. These include utilizing vibration (e.g. ultrasonics, through the delivery of a second cannula or probe, for example, through the second pedicle) or physical compaction (e.g. using a curved probe or tamp through a pedicle path or with an internal or external sheath. Compaction may be particularly useful when filling hard tissue cavities such as bone cavities.

Closing a Cavity

A cavity opening through which an implant was inserted may be closed and/or sealed to maintain the compaction, and to prevent the loss of implant material from the cavity. After filling and/or distracting a cavity, a user may cut the implant and remove the applicator cannula. FIG. 8C shows that the user may also block 802 or otherwise close the opening into the bone cavity, for example, by the local application of a cement material through the cannula (or another cannula). Other methods for closing the void may include tapered pins, screws with blunt head and tip, or even screws with compressible tip members such as a spring to absorb, minimize, or prevent settling of the implant.

Figure 9A:
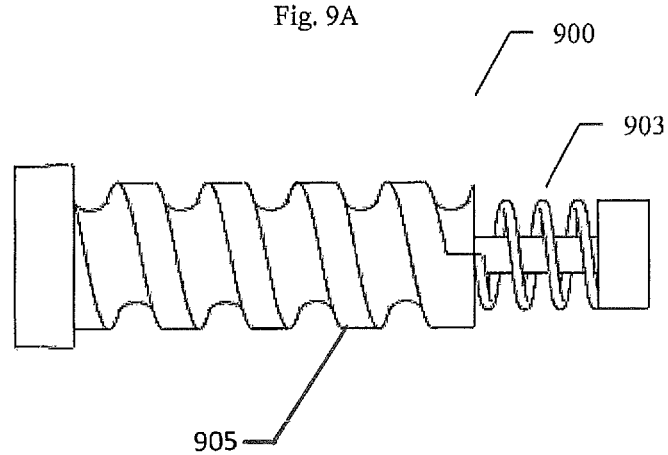
FIGS. 9A and 9B show a screw closure compatible with the implants and applicators described herein.
Figure 9B:
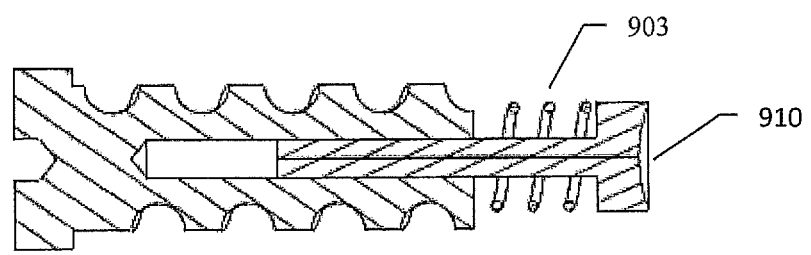

FIG. 9 shows an example of a screw closure 900 for use with an implant that comprises a spring 903 for applying pressure to an implant within a cavity. The screw includes threads 905. After distracting and/or filling a hard tissue cavity as described, the screw closure is screwed into the opening through which the implant was inserted. The spring-loaded tip 910 of the screw is blunt, and applies pressure onto the inserted implant. Thus, the screw can minimize any settling or further compaction that may occur after the insertion of the implant by applying pressure to help keep the implant compacted.

In general, implants and applicators as described herein may be used for filling cavities that do not require distraction.

A secondary filling material may also be used. For example, when filling a bone cavity, fluent bone filler may also be used to the cavity in addition to the solid implant. The combination of hard segment and fluid filler may provide added stability. The fluent material (e.g. cement) may also harden into a solid. In addition, the implant segments may reduce leakage of additional bone filler (such as bone cement) by blocking openings in the cavity that fluent filler would otherwise leak through. Less fluent filler may be needed if it is used after the solid implant, further reducing the risk of harmful leakage. In one variation, secondary filling material may be applied in conjunction with an expandable membrane around the implant segments, preventing any substantial leakage from the bone cavity.

In general, the implants and/or applicators described herein may be used to distract a cavity without being left in the cavity after distraction. For example, an implant may be used to create or enlarge a cavity. In one example, an implant may be inserted into a body region void to expand the void. The surfaces of the body region void will be compressed by the implant, causing it to expand. After removing the implant, the cavity may remain expanded, facilitating further procedures (e.g. insertion of additional devices or materials, etc). Similarly, a hard tissue cavity such as a bone cavity may be enlarged or reshaped by inserting an implant which can then be removed or left within the non-soft tissue cavity.

It may be desirable to leave the implant in the tissue for an extended period of time up to and including the lifetime of the patient. In one variation, the implant is a permanent implant for filling and/or distracting body regions to provide long-term support and shape to the body region. In one variation, the implant is intended to be used for a period of at least six months. In one variation, the implant is intended to be used for a period of at least a year. In one variation, the implant is intended to be used for a period of many years. Implants intended for long-term use may be made of materials which do not lose a significant amount of their strength or shape over time after implantation. In some variations, the implant could be used for short term (e.g., less than 6 months, less than 6 weeks, less than a week, less than an day, less than an hour, etc.).

Securing a Fastener

Figure 21:
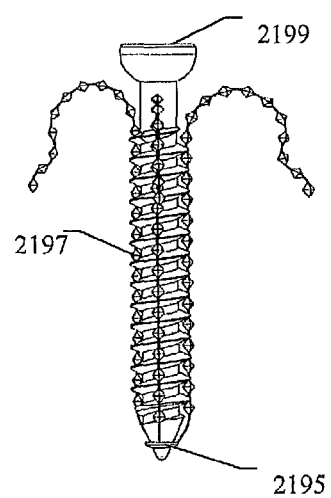
FIG. 21 shows a locking device including an anchor.

The implants and/or applicators described herein may be used to secure another implant, including fastening devices. For example, a bone screw may be inserted into an implant filling a bone cavity. Alternatively, and implant may be used to secure (or to help secure) fastening devices by coupling with the fastening device. FIG. 21 shows one variation of an implant configured to help secure a fastening device (shown as a screw). In FIG. 38, the implant is configured as an anchor that fits between the side of the fastening device and the site into which the fastening device is being inserted (e.g., a non-soft tissue such as bone). In some variations, the implant comprises a coupler (e.g., a loop, ring, hook, etc.) to couple the implant to the fastening device. Any appropriate coupler that can secure at least a portion of the implant to the fastening device may be used. The implant is coupled to the fastener so that the implant (e.g., the segments of the implant) comes between the fastening device and the site of insertion (e.g., the wall of the cavity into which the fastener is being secured).

As the fastener is secured into the body distally (e.g., into bone), the implant becomes lodged between the fastening device and the wall of the structure into which the fastener is being inserted. Thus, the implant helps anchor the fastening device. In some variations, the implant may be slightly compressible, or some of the segments may be compressible. In some variations, some of the segments (or all of them) are frangible, and may rupture under the stress of insertion to help secure the fastener into position. Some of the segments may rupture and release a bonding agent, or a catalyst to activate a fluent material or bonding agent that is included with the implant (or added to the implant), causing it to harden and further secure the fastener in position.

The implant may be connected at the distal end with several chains of segments delivered simultaneously delivered surrounding a bone screw as shown in FIG. 21. This may be particularly useful when it is desirable to use a bone screw in weakened (e.g. osteoporotic or necrotic) bone tissue. In another variation, the implant described herein may be inserted to secure an existing implant.

Hybrid Ram Applicator

FIGS. 11 to 16 describe one variation of an applicator as described above. The hybrid ram applicator shown in FIGS. 11 to 16 combines many of the features and elements described above, and allows micro-insertion, micro-retraction, macro-insertion, and macro-retraction of some variations of the implants described above. The hybrid ram applicator may be particularly useful for applying implants into vertebral cavities, or for any cavity appropriate to receive a segmented implant as described herein.

The hybrid ram 2800 shown in FIG. 11 is composed of three primary components. First, an internal cannula 2801 (see FIGS. 12A, 13 and 14) component that is cylindrical, with two intersecting cylindrical channels running down its length. The lower channel contains a chain of implants 2810 as described above. It also contains a cannula 2812 protruding from its far end that is axially aligned with the chain of implants in the internal cannula.

Second, the hybrid ram includes a stiff member, configured as a reciprocating ram 2803 (see FIGS. 12B, and 15A-15B) that is inserted into the upper channel of the internal cannula 2801. The stiff member includes a releasable engagement region for releasably engaging at least a region of the implant. In the example shown in FIGS. 11 to 16, the stiff member is configured as a reciprocating ram that has a releasable engagement region having radial grooves 3201 (e.g., "teeth") on at least one radial portion of the length of the reciprocating ram that can engage with the implant chain 2810 in the lower channel of the internal cannula 2801. Another radial portion of the length of the reciprocating ram includes a long axial groove 2814. When the reciprocating ram is engaged with the implant in the radial grooves 3201, by sliding the reciprocating ram along the axis of the upper channel in the internal cannula, segments of the implant can be pushed or pulled down the channel, and out (or into) the cannula at the end of the applicator, thereby inserting or retracting implant segments.

As the reciprocating ram slides forward, a cylindrical channel along the long axis of the reciprocating ram gradually mates with a guide pin 18f (shown in FIGS. 13A and 13B) that is fixed on the rotational axis of the internal cannula, which linearly aligns the implant. After sliding the reciprocating ram to its furthest extent, it can be rotated axially so that the radial grooves rotate away from the implant segments, and the long axial groove abuts the implant instead. Since the continuous axial groove does not engage (or contain) the individual segments, axial movement of the reciprocating ram does not move the implant. The axial groove only provides axial captivation of the implant chain, allowing the reciprocating ram to be retracted to its initial position without advancing or retracting the implant. The reciprocating ram can then be rotated to move the radial grooves into contact with the implant segments, so that the reciprocating ram can re-capture another length of the remaining implant chain and insert additional implants into the vertebral body. When desired elevation of the vertebral body is achieved, the reciprocating ram can once again be rotated to captivate the implant chain in the long axial groove. Once in this position, a simple ram may be inserted into the reciprocating ram through an opening in the handle 3205 (in FIG. 15A) thus allowing further manual compaction of the implants in the vertebral body.

The internal cannula is housed in a third component, an outer sheath 2805 (see FIGS. 12C and 16A) that allows for ergonomic control of the implant delivery process. The outer sheath contains a cylindrical channel along its center axis that contains the internal cannula. During the implant delivery, the depth in the vertebral body at which implant ejection occurs can be varied by translating the internal cannula along the internal void of the outer sheath. A specific depth can be maintained (e.g., in 5 mm increments) by virtue of a dual-mode locking pin (see FIGS. 12D and 16B) on the outer sheath that mates with radial grooves along the outer diameter of the internal cannula.

In summary, the described implants, applicators and methods of using them may be used to fill and/or distract a non-soft tissue including a bone cavity, in particular a vertebral compression fracture. The implant may achieve many advantages not realized with other devices intended to fill and/or distract a bone cavity. In particular, the implant described herein substantially reduces the chance of harmful leakage of bone filler material and provides three-dimensional support to the bone cavity.

Although the above examples have described primarily the filling of bone and other non-soft tissue cavities, particularly within the intervertebral body, and for treatment of vertebral compression fractures, the implants, applicators and methods described herein may be used on any tissue cavity, including but not limited to those arising from trauma, fractures, non-unions, tumors, cysts, created by a pathology or by the action of a surgeon. It will be appreciated by persons skilled in the art that numerous variations and/or modifications may be made to the described device as specifically shown here without departing from the spirit or scope of that broader disclosure. The various examples are, therefore, to be considered in all respects as illustrative and not restrictive.

I claim:

1. An implant for insertion into a cavity in a body tissue, comprising:
a plurality of flexibly connected segments, each segment being flexibly connected to an immediately adjacent segment by a flexible connecting member configured to transmit motion between immediately adjacent segments in a manner enabling directional filling of the cavity with the implant, and the flexible connecting member including biological properties including at least one of medicinal properties, antibiotic properties, analgesic properties, anticoagulant properties, bone growth enhancing properties, or cell or gene therapies
wherein at least some of the segments are frangible and configured to rupture upon engagement with the body tissue during insertion.

2. The implant of claim 1, one or more of the segments having a medicinal agent including a bone-growth promoting agent.

3. The implant of claim 2, the medicinal agent including at least one of a bone derived growth factor (BDGF), a bone morphogenetic protein (BMP), an antibacterial agent, an antiviral agent, a vascularizing agent, an analgesic, an anticoagulant, a cell therapeutic agent, and a gene therapeutic agent.

4. The implant of claim 1, comprising a flexible tube having an inner region, the segments being arranged within the inner region.

5. The implant of claim 4, the flexible tube having a first dimension located at each of the segments and a second dimension located between adjacent pairs of segments, the first dimension being greater than the second dimension so that the flexible tube has an undulating shape.

6. The implant of claim 1, each of the segments including a pellet secured to the flexible connecting member in such a manner that the pellet is not rotatable relative to the flexible connecting member.

7. The implant of claim 1, each of the pellets including at least one of: (a) a hole therethrough through which the associated flexible connecting member is threaded, (b) one or more attachments sites to which the associated flexible connecting member is tied or otherwise attached, (c) one of a track or a groove that mates to the associated flexible connecting member, (d) an adhesive attaching the pellet to the associated flexible connecting member, or (e) a crimped or swaged attachment to the flexible connecting member.

8. The implant of claim 1, each of the segments having a compressive strength greater than about 20 MPa.

9. The implant of claim 1, at least some of the segments being porous to facilitate tissue in-growth.

10. The implant of claim 1, wherein at least some of the segments have a diameter within a range of 1 to 10 mm.

11. The implant of claim 1, comprising a fluent settable agent having biological properties.

12. The implant of claim 1, comprising a fluent material that does not harden after the implant is inserted into the cavity in the body tissue.

13. The implant of claim 1, the implant being insertable into at least one of a bone, bone marrow, a vertebral body, an intervertebral body, a spinal disk, a tibial plateau, a femoral head, a hip bone, a ligament, cartilage, scar tissue, mineralized tissue, calcified tissue, a tumor, a cyst or a tissue cavity having at least one hard surface.

14. The implant of claim 1, the implant being configured to distract the cavity in the body tissue.

15. The implant of claim 1, one or more of the segments having one of a spherical shape, a cylindrical shape, a bullet shape, a conical shape, a rectangular shape, or a polygonal shape.

16. An implant for insertion into a cavity in a body tissue, comprising:
a plurality of flexibly connected segments, each segment being flexibly connected to an immediately adjacent segment by a flexible connecting member configured to transmit motion between immediately adjacent segments in a manner enabling directional filling of the cavity with the implant, and the flexible connecting member including biological properties including at least one of medicinal properties, antibiotic properties, analgesic properties, anticoagulant properties, bone growth enhancing properties, or cell or gene therapies;
a flexible tube having an inner region, the segments being arranged with in the inner region; and
at least one of the segments possessing a plurality of protrusions that perforate the flexible tube during insertion of the implant into the cavity of the implant into the cavity.

* * * * *